US012042544B2

(12) United States Patent
Khang et al.

(10) Patent No.: US 12,042,544 B2
(45) Date of Patent: Jul. 23, 2024

(54) STEM CELL-NANO DRUG DELIVERY SYSTEM COMPLEX, USE THEREOF AND METHOD FOR PREPARING THE SAME

(71) Applicant: GACHON UNIVERSITY OF INDUSTRY-ACADEMIC COOPERATION FOUNDATION, Seongnam-si (KR)

(72) Inventors: Dong Woo Khang, Seoul (KR); Yeon Kyung Lee, Incheon (KR); Sang-Woo Kim, Incheon (KR); Jun-Young Park, Seoul (KR)

(73) Assignee: GACHON UNIVERSITY OF INDUSTRY-ACADEMIC COOPERATION FOUNDATION, Seongnam-si (KR)

( * ) Notice: Subject to any disclaimer, the term of this patent is extended or adjusted under 35 U.S.C. 154(b) by 717 days.

(21) Appl. No.: 15/957,405

(22) Filed: Apr. 19, 2018

(65) Prior Publication Data
US 2018/0303954 A1   Oct. 25, 2018

(30) Foreign Application Priority Data

Apr. 19, 2017 (KR) .................. 10-2017-0050693
Apr. 21, 2017 (KR) .................. 10-2017-0051864

(51) Int. Cl.
| | | |
|---|---|---|
| *A61K 9/00* | (2006.01) | |
| *A61K 41/00* | (2020.01) | |
| *A61K 47/52* | (2017.01) | |
| *A61K 47/68* | (2017.01) | |
| *A61K 47/69* | (2017.01) | |
| *A61P 35/00* | (2006.01) | |
| *C07K 16/28* | (2006.01) | |
| *A61K 39/00* | (2006.01) | |

(52) U.S. Cl.
CPC ...... *A61K 47/6901* (2017.08); *A61K 41/0047* (2013.01); *A61K 47/52* (2017.08); *A61K 47/6803* (2017.08); *A61K 47/6849* (2017.08); *A61K 47/6923* (2017.08); *A61K 47/6929* (2017.08); *A61P 35/00* (2018.01); *C07K 16/2803* (2013.01); *C07K 16/2896* (2013.01); *A61K 2039/505* (2013.01)

(58) Field of Classification Search
CPC .................................................. A61K 47/6901
See application file for complete search history.

(56) References Cited

FOREIGN PATENT DOCUMENTS

KR    1020140026896 A    3/2014

OTHER PUBLICATIONS

Sun, Cancer stem cell therapy using doxorubicin conjugated to gold nanoparticles via hydrazone bonds, Biomaterials, 2014, 35, 836-845.*

(Continued)

*Primary Examiner* — Paul W Dickinson
(74) *Attorney, Agent, or Firm* — ArentFox Schiff LLP

(57) ABSTRACT

Provided are a stem cell-nano anticancer drug complex in which an anticancer drug based on carbon nanotubes (CNT) and gold (Au) nano particles is loaded on the surface of stem cells, which can overcome side effects of conventional stem cells and targeting limitations of nano anticancer drugs and whose anticancer effect is very excellent, the use thereof, and a method for preparing the same.

14 Claims, 27 Drawing Sheets

(56) References Cited

OTHER PUBLICATIONS

Muddineti, Current trends in using polymer coated gold nanoparticles for cancer therapy, International Journal of Pharmaceutics, 2015, 484, 252-267.*

Patel, Graphene-based platforms for cancer therapeutics, Ther. Deliv. (2016) 7(2), 101-116. (Year: 2016).*

Lalwani, Three-dimensional carbon nanotube scaffolds for long-term maintenance and expansion of human mesenchymal stem cells, Journal of Biomedical Materials Research A, 2017, 105A, Issue 8, 1927-1939. (Year: 2017).*

Kumar, Multiple Roles of CD90 in cancer, Tumour Biol., Sep. 2016, 37(9), 11611-11622; Abstract only (Year: 2016).*

Min Li et al., "Nanoparticles and mesenchymal stem cells: a win-win alliance for anticancer drug delivery", Apr. 7, 2016, 36910-36922, RSC Adv, 6, 2016.

Kang et al., Mesenchymal Stem Cells Aggregate and Deliver Gold Nanoparticles to Tumors for Photothermal Therapy, American Chemical Society, Sep. 8, 2015, https://pubs.acs.org/doi/10.1021/acsnano.5b02207.

Abir O El-Sadik et al., Nanoparticle-labeled stem cells: a novel therapeutic vehicle, Clinical Pharmacology: Advances and Applications, Mar. 12, 2010.

* cited by examiner

STEM CELL-NANO DRUG DELIVERY SYSTEM COMPLEX, USE THEREOF AND METHOD FOR PREPARING THE SAME

CROSS-REFERENCE TO RELATED APPLICATION

This application claims priority of Korean Patent Application No. 10-2017-0050693 filed on Apr. 19, 2017 and Korean Patent Application No. 10-2017-0051864 filed on Apr. 21, 2017, the contents of each of which are incorporated by reference.

BACKGROUND

The present disclosure relates to a nano-drug delivery system complex, and more particularly, to a stem cell-nano drug delivery system complex and the use thereof.

At present, although surgical treatment, radiation therapy, and treatment through administration of anticancer drugs, etc. are available as methods for treating cancer, these methods are accompanied with side effects or procedures are limited depending on the degree of cancer progression. In particular, as a result of repeated research, types of anticancer drugs have increased quantitatively, but there was no significant change in terms of quality. The reason therefor is that most of anticancer drugs function as a mechanism to stop the cell cycle of cells that are actively dividing and kill them, and in this regard, anticancer drugs attack cells that are normally dividing in addition to cancer cells, thereby inducing hair loss, loss of appetite, and reduction of immunity due to leukopenia, etc., which are typical side effects of anticancer drugs. In order to minimize side effects of these anticancer drugs, the development of target anticancer drugs has been actively carried out, and at present, 18 or more target anticancer drugs have been developed and clinically applied, and more than 200 types are in clinical trials. However, even for the same kind of cancer, these target anticancer drugs have a limitation in that they are effective for patients in which a specific target factor is exhibited. Since it is necessary to administer target therapeutic agents over a long period of time, there is a problem of inducing tolerance, and in order to complement this, there are methods such as cocktail therapy of concurrently administering a target therapeutic agent with conventional strong anticancer drugs, a method of using a single anticancer drug for removing cancer in a short amount of time by simultaneously attacking various target factors, etc. These methods also involve the risk of inducing serious side effects. Therefore, for target therapeutic agents that can cure cancer efficiently while having fewer side effects, research on anticancer drugs utilizing gold nanoparticles, biodegradable polymers, and carbon nanotubes is actively being conducted. In particular, nanoparticles can be applied in various biomedical fields including imaging, cancer treatment, etc., due to mechanical, visual, and chemical properties. As for carbon nanotubes as anticancer drug carriers, research is mainly conducted related to a method of effectively delivering biological molecules into cells via endocytosis, and a method of treating the surface of carbon nanotubes with polyethylene glycol (PEG) and loading anticancer drugs is also currently being researched. In addition, when gold particles are controlled to a nanoscale, new physicochemical properties that cannot be observed in original materials are displayed, and this is because the proportion of surface atoms significantly increases as the size of crystals decreases, which results in significant changes in the thermodynamic properties of materials. In general, surface atoms of solid materials contribute greatly to free energy compared to internal atoms, and an increase in surface atoms change thermodynamic properties such as melting point lowering and phase transition of nanocrystals, and since this exhibits electromagnetic, optic, mechanical, and thermal properties, nanoscale gold particles can be basic materials for various nano elements such as transistors, light emitting devices, sensors, solar cells, etc., and these particles are used for the preparation of anticancer drugs with improved efficiency. For example, research on anticancer drugs based on gold nanoparticles in which a functional group is added to a gold nanoparticle, and an anticancer drug such as doxorubicin and paclitaxel are loaded on the surface of gold nanoparticles are actively conducted.

In the case of conventional nano anticancer drugs that have been developed for more efficient chemotherapy, biodegradable polymers that have been used in formulations are limited with respect to delivering anticancer drugs to target sites due to anticancer drugs being easily dissociated from nanomaterials under acidic pH and blood conditions. Non-degradable nanoparticles such as silica, magnetic particles, carbon-based nanoparticles, etc. are not verified for their efficacy at an anticancer drug dose at which toxicity can be overcome, and there are disadvantages of being accumulated in the reticular endothelial system (RES) organ, etc. Overall, there are still difficult problems for which researchers should solve related to conventional nano anticancer drugs. In this regard, Korean Registered Patent No. 1711127 discloses a cancer-targeting iron oxide nanoparticle complex bound with an anticancer drug, the preparation method of the same, and the use thereof.

However, in the case of the related art, there is a problem in that the effect of the anticancer drug decreases due to low cancer targeting ability.

SUMMARY OF THE INVENTION

The present invention is aimed to solve various problems including the problems above and to provide a new form of a stem cell-nano anticancer drug system complex, the use thereof, and a method for preparing the same, which overcomes the targeting limitation of conventional nano anticancer drugs and maximizes the efficacy of anticancer drugs. However, these aims are exemplary, and the scope of the present invention is not limited thereto.

According to an aspect of the present invention, a stem-cell nano anticancer drug complex in which a carbon nanotube (CNT) or gold (Au) nanoparticle loaded with an anticancer drug is bound to a surface of a stem cell is provided.

According to another aspect of the present invention, a pharmaceutical anticancer composition which contains the stem cell-nano anticancer drug complex as an active ingredient is provided.

According to another aspect of the present invention, a method for treating cancer, including administering a therapeutically effective amount of the stem cell-nano anticancer drug complex to a subject suffering from cancer is provided.

According to an aspect of the present invention, a method for preparing a stem cell-nano anticancer drug complex, including preparing a carboxylated nanoparticle by introducing a carboxyl group (—COOH) on the surface of a nanoparticle; preparing an EDC {1-Ethyl-3-(3-dimethylaminopropyl)carbodiimide} linker bound nanoparticle by linking the EDC to the carboxylated nanoparticle; binding an anticancer drug and an antibody, a functional fragment of the antibody or an antibody mimetic that specifically binds to a stem cell surface marker protein to the EDC linker bound nanoparticle covalently; and attaching an anticancer drug and an antibody, a functional fragment of the antibody or an antibody mimetic specific to the stem cell surface marker protein bound nanoparticle to the stem cell is provided.

According to an embodiment of the present disclosure, a new form of a stem cell-nano anticancer drug complex can be realized, which may maximize the efficacy of the anticancer drug and enhance the targeting ability of conventional nano anticancer drugs. However, the scope of the present invention is not limited to these effects.

BRIEF DESCRIPTION OF THE DRAWINGS

Exemplary embodiments can be understood in more detail from the following description taken in conjunction with the accompanying drawings, in which.

DETAILED DESCRIPTION OF EMBODIMENTS

Figure 1:
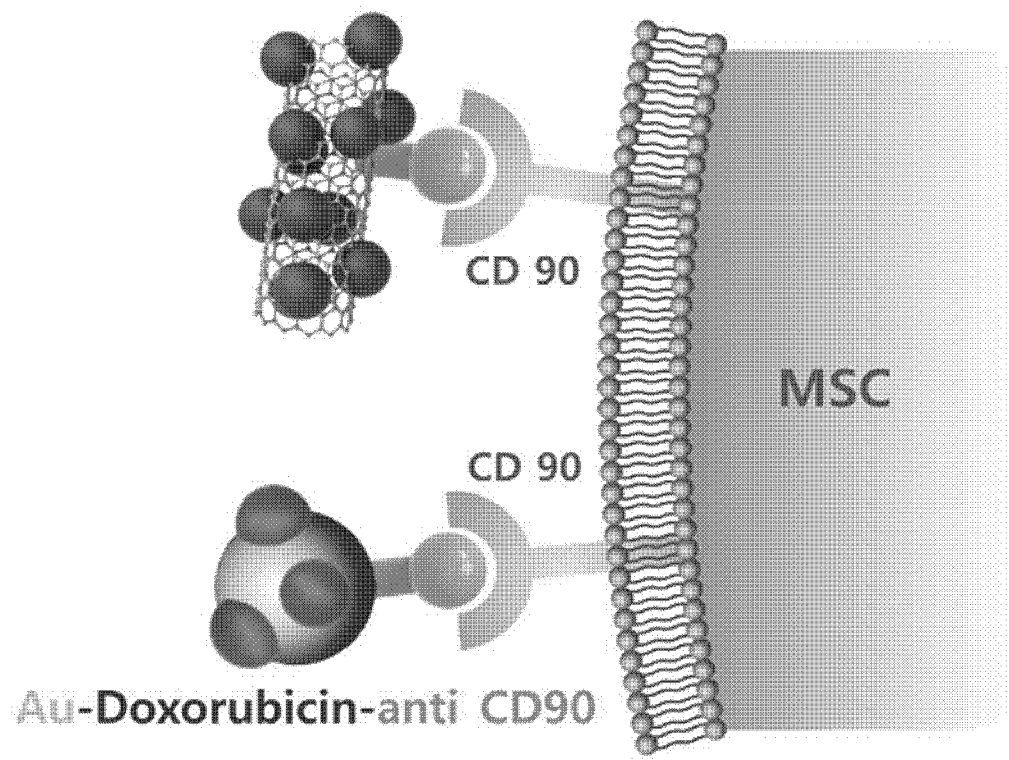
FIG. 1 is a diagram which schematically illustrates the preparation of a stem cell-nano anticancer drug complex in which a carbon nanotube (CNT)-based and gold (Au) nano-based anticancer drug is loaded on a surface of a mesenchymal stem cell (MSC), in accordance with an exemplary embodiment.

Hereinafter, specific embodiments will be described in detail with reference to the accompanying drawings.

Definition of Terms:

The term "mesenchymal stem cells (MSC)" as used in this document refers to adult mesenchymal stem cells (MSCs) among adult stem cells, and includes differentiation derived from bone marrow, umbilical cord blood, adipocytes, and it is characterized by having multi-differentiation ability.

As used in this document, the term "carbon nanotube (CNT)" is a carbon allotrope composed of a large amount of carbon present on the earth, one carbon atom is bonded to another carbon atom with a hexagonal honeycomb pattern to form a tube, and it refers to a substance in the form of a substance in a very small area at the level where the tube diameter is nanometer (nm=one billionth of a meter).

The carbon nanotubes have excellent mechanical properties, electrical selectivity, excellent field emission characteristics, high efficiency hydrogen storage medium characteristics, etc., as existing perfect new materials with almost no defects, and it is manufactured by a high-level synthesis technique, and examples of a synthesis method include an electric discharge method, a thermal decomposition method, a laser vapor deposition method, a plasma chemical vapor deposition method, a thermal chemical vapor deposition method, an electrolysis method, a Flame synthesis method and so on.

The term "gold nanoparticle (AuNP)" as used in this document means that when the particle size of gold is in the nanometer scale, it is not perfect spherical with particles of about 1-9 m, it is in an irregular shape, each shape Depending on the size and size, the states are different and the colors are different. The color is determined depending on whether the wavelength corresponding to an arbitrary region is reflected and absorbed to some extent according to the states. Thus, energy gap can be inferred, and the larger the size, the more anticancer drug is attached to give shorter wavelength color, the particle is used as an agent that carries particles or the specific antibody is attached, it can be used to detect antigens on the surface. It can also be used as a remedy for rheumatoid arthritis and is a next generation new substance that can be used not only in the medical field but also in various fields.

The term "nano anticancer drug complex" as used in this document refers to a substance that controls the release and absorption of an anticancer drug, and targets and transmits an anticancer drug to a specific site in the body It is intended to maximize efficacy while reducing the side effects of anticancer drugs and to adjust the necessary amount of anticancer drug to stay at the target site effectively for a certain period of time, meaning anticancer drug delivery system using nanotechnology.

The phrase "carbon nanotube (CNT) or gold (Au) nanoparticles loaded with an anticancer drug" as used in this document means an anticancer drug-nanoparticle complex in which a functional group, such as a carboxyl group (—COOH), is incorporated in carbon nanotubes or gold nanoparticles, and an antibody for chemotherapy, such as Trastuzumab, Adalimumab and Infliximab, or an anticancer chemotherapeutic compound, such as doxorubicin and paclitaxel, is attached to the surface of nanoparticles. The introduction of the functional group in the carbon nanotube may be carried out by acid treatment and the introduction of the functional group in the gold particle may be carried out by coating biocompatible polyester polymers such as carboxylated PEG or PLGA in order to stabilize them electrostatically, since the gold nanoparticles do not have functional groups themselves. After the coating, an anticancer chemotherapeutic agent having an amine group (—NH$_2$) such as doxorubicin or an antibody may be attached to carboxylated gold nanoparticles.

The term "functional fragment of an antibody" as used herein means a fragment of an antibody in which the function of an antigen binding site of an antibody is preserved so that the antibody has antigen binding ability. Functional fragments of these antibodies include cleaving fragments of proteolytic enzymes such as Fab, Fab', and F(ab')$_2$ produced by cleaving antibodies with proteolytic enzymes such as papain or pepsin, and also include recombinant antibody fragments produced by genetic recombination such as Fv, scFv, diabody, triabody, and sdAb.

The term "Fab" as used in this document means fragments of V$_H$-CH1 and V$_L$-C$_L$ produced by cleaving an antibody molecule, as an antigen-binding antibody fragment (fragment antigen-binding), with a proteolytic enzyme papain. The other two fragments produced by papain are called Fc (fragment crystallizable).

The term "F(ab')$_2$" as used in this document is a fragment containing an antigen binding site among fragments generated by cleaving an antibody with pepsin, which is a proteolytic enzyme, and has the form of a tetramer in which two of the Fabs are connected by a disulfide bond. The other fragment generated by pepsin is called pFc'.

The term "Fab" as used in this document is an antibody fragment having the same structure as Fab described above, is produced by reducing F(ab')$_2$, and has a slightly longer heavy chain portion than Fab.

The term "scFv", as used herein, is an acronym for single chain fragment variable and means a recombinant antibody fragment prepared as a single chain by linking two variable regions (V$_H$ and V$_L$) of the Fab with a linker peptide.

The term "sdAb (single domain antibody)" as used in this document is also called a nanobody and means an antibody fragment composed of a single variable region fragment of an antibody. Although sdAb derived from the main chain is used, it has been reported that a single variable region fragment derived from the light chain is also specifically bound to the antigen.

As used herein, the term "$V_HH$" refers to a variable region fragment of a heavy chain of IgG derived from camelids that consist of only two heavy chains. The $V_HH$ is the smallest (~15 kD) antibody fragment capable of binding to antigen. and has been developed by Ablynix Nv under the tradename Nanobody®.

The term "Fv (fragment variable)" as used in this document refers to a dimeric antibody fragment consisting solely of a heavy chain fragment ($V_H$) and a light chain fragment ($V_L$) of an antibody whose size (~25 kD) is between those of sdAb and Fab. It is prepared by hydrolyzing an antibody under special conditions, or by expressing the genes encoding $V_H$ and $V_L$ by inserting the genes into one expression vector.

The term "diabody" as used herein means a divalent and bispecific recombinant antibody fragment prepared by dimerizing two scFvs by shortening the length of a linker peptide (5 a.a.) between VH and VL, and is known to have higher antigen specificity than typical scFvs.

The term "triabody" as used herein refers to a trivalent recombinant antibody fragment produced so that three scFvs form a trimer.

The term "antibody mimetics" as used herein are single chain-based proteins that are capable of specifically binding to an antigen like an antibody. They are screened by panning after random mutagenesis in the antigen recognition site of underlying scaffold proteins. These antibody mimetics include, but are not limited to, affilins (Ebersbach, H. et al. *J. Mol. Biol.*, 372: 172-185, 2007), affimers (Johnson, A. et al., *Anal. Chem.*, 84(15): 6553-6560, 2012), affitins (Kerhenbrink, M. et al., *J. Mol. Biol.*, 383: 1058- 1068, 2008), anticalins (Skerra, A. et al., *FEBS J.* 275: 2677-2683, 2008), avimers (Silverman, J. et al. *Nat. Biotechnol.*, 23: 1556-1561, 2005), DARPin (Stumpp, M. T. et al., *Drug Discov. Today* 13 (15-16): 695-701, 2008), Fynomers (Grabulovski, D. et al., *J. Biol. Chem.* 282 (5): 3196-3204, 2007), monobodies (Koide, A. et al., *Methods Mol. Biol.*, 352: 95-109, 2007), VLRs (variable lymphocyte receptors; Boehm, T. et al., *Annu. Rev. Immunol.* 30: 203-220, 2012), repebodies (Lee, S.-C. et al., *Proc. Natl. Acad. Sci. USA* 109 (9): 3299-3304, 2012) and the like.

DETAILED DESCRIPTION OF THE INVENTION

According to one aspect of the present invention, a stem cell-nano anticancer drug complex in which a carbon nanotube (CNT) or a gold (Au) nanoparticle loaded with an anticancer drug is attached to the surface of the stem cell is provided.

In the stem cell-nano anticancer drug complex, the carbon nanotube may be a multi-wall carbon nanotube, and the multi-wall carbon nanotube may have a diameter of 5 to 50 nm.

In the stem cell-nano anticancer drug complex, the carbon nanotube or gold nanoparticle is attached to an antibody, a functional fragment of the antibody or an antibody mimetic which binds to a stem cell surface marker protein specifically. The functional fragment of the antibody may be Fab, $F(ab')_2$, Fab', scFv, Fv, $V_HH$ (variable domain of camelid heavy chain), sdAb, diabody or triabody, and the antibody mimetic may be Affibody, Affilin, Affitin, Anticalin, Avimer, DARPin, Fynomer, monobody, VLR (variable lymphocyte receptor) or repebody. The stem cell surface marker protein may be CD90, CD73 or CD105.

In the stem cell-nano anticancer drug complex, the weight ratio of the carbon nanotube to the anticancer drug in the complex may be 1:1 to 1:3, and the anticancer drug may be doxorubicin, paclitaxel, ABT 737, 5-fluorouracil, BCNU, CCNU, 6-mercaptopurine, nitrogen mustard, cyclophosphamide, vincristine, vinblastine, cisplatin, methotrexate, cytarabine, thiotepa, busulfan, or procarbazine. The stem cell may be adipose stem cell, umbilical cord blood stem cell, induced pluripotent stem cell, or mesenchymal stem cell (MSC).

In the stem cell-nano anticancer drug complex, the gold nanoparticle may be coated with a polymeric substance having a carboxyl group, and the polymeric substance having a carboxyl group may be carboxylated PEG (polyethylene glycol), hyaluronic acid, PHA (polyhydroxyalkanoates), PLGA {poly(lactic-co-glycolic acid)}, PLA {poly(lactic acid)} or PGA {poly(glycolic acid)}.

According to another aspect of the present invention, a pharmaceutical anticancer composition comprising the stem cell-nano anticancer drug complex as an active ingredient is provided.

According to another aspect of the present invention, a method of treating cancer comprising: administering a therapeutically effective amount of the stem cell-nano anticancer drug complex to a subject suffering from cancer is provided.

The pharmaceutical composition of the present invention may include a pharmaceutically acceptable carrier. Although the compositions containing a pharmaceutically acceptable carrier may be in various dosage forms, such as oral or parenteral, a formulation for parenteral administration is desirable. When formulated, the composition is prepared using commonly used diluents or excipients such as fillers, bulking agents, binders, wetting agents, disintegration agents, surfactants and the like. The solid preparation for oral administration includes tablets, pills, powders, granules, capsules and the like, and these solid preparations contain at least one excipient of one or more compounds, for example, starch, calcium carbonate, sucrose or lactose, gelatin and the like. Besides simple excipients, lubricants such as magnesium stearate and talc can also be used. As liquid preparations for oral administration, suspensions, internal solutions, emulsions, syrups and the like are applicable. In addition to water and liquid paraffin, which are commonly used simple diluents, various excipients such as wetting agents, sweeteners, fragrances, preservatives, and the like may be included. Formulations for parenteral administration include sterile aqueous solutions, nonaqueous solvents, suspensions, emulsions, lyophilized preparations, and suppositories. The nonaqueous solvents and suspension solvents may be propylene glycol, polyethylene glycol, vegetable oils such as olive oil, injectable esters such as ethyl oleate, and the like. As the suppository base, Witepsol, macrogol, tween 61, cocoa butter, laurin fat, glycerogelatin and the like may be used.

The above-mentioned pharmaceutical anticancer composition may be in the form of any one selected from the group consisting of a tablet, pill, powder, granule, capsule, suspension, solution, emulsion, syrup, sterilized aqueous solution, nonaqueous solvent, emulsion, freeze-dried preparation and suppository.

The pharmaceutical anticancer composition of the present invention can be administered orally or parenterally. When administered parenterally, it can be administered via various administration routes such as intravenous injection, intranasal inhalation, intramuscular administration, intraperitoneal administration and percutaneous absorption.

The above-described composition of the present invention is administered in a pharmaceutically effective amount.

The term "pharmaceutically effective amount" as used herein means an amount sufficient to treat a disease at a reasonable benefit/risk ratio applicable to medical treatment and the level of the effective amount may be determined according to factors including the type of subject, severity, age, sex, activity of anticancer drug, sensitivity to anticancer drug, administration time, route of administration and rate of excretion, duration of treatment, other anticancer drugs used in combination, and others factors well-known in the medical field. The pharmaceutical composition of the present invention may be administered in a volume of 0.1 mg/kg to 1 g/kg, more preferably 1 mg/kg to 500 mg/kg. The dosage can be appropriately adjusted depending on the age, sex and condition of the patient.

The pharmaceutical anticancer composition of the present invention may be administered as an individual therapeutic agent or in combination with other anticancer drugs, and may be administered sequentially or simultaneously with other conventional anticancer drugs. It may also be administered as single or multiple doses. It is important to administer an amount that can obtain the maximum effect with minimal side effects considering all of the above factors, and said amount may be readily determined by those skilled in the art.

According to an aspect of the present invention, a method for preparing a stem cell-nano anticancer drug complex, including preparing a carboxylated nanoparticle by introducing a carboxyl group (—COOH) on the surface of a nanoparticle; preparing an EDC {1-Ethyl-3-(3-dimethylaminopropyl)carbodiimide} linker bound nanoparticle by linking the EDC to the carboxylated nanoparticle; binding an anticancer drug and an antibody, a functional fragment of the antibody or an antibody mimetic that specifically binds to a stem cell surface marker protein to the EDC linker bound nanoparticle covalently; and attaching an anticancer drug and an antibody, a functional fragment of the antibody or an antibody mimetic specific to the stem cell surface marker protein bound nanoparticle to the stem cell is provided.

In the method for producing a stem cell-nano anticancer drug complex, the nanoparticle may be a carbon nanotube, the carbon nanotube may be a multi-walled carbon nanotube, and the multi-walled carbon nanotube may have a diameter of 5-50 nm.

In the above-mentioned method for producing a stem cell-nano anticancer drug complex, the preparing of the carboxylated nanoparticle may be carried out by treating the carbon nanotube with an acid. The method may further include applying ultrasonic waves to the acid-treated carbon nanotube.

In the above-mentioned method for producing a stem cell-nano anticancer drug complex, the nanoparticle can be a gold nanoparticle, and the preparing of the carboxylated nanoparticle may be performed by a polymer coating process of coating the gold nanoparticle with a polymer containing a carboxyl group. The polymer containing a carboxyl group may be a carboxylated polyethylene glycol, hyaluronic acid, PHA (polyhydroxyalkanoates), PLGA {poly(lactic-co-glycolic acid)}, PLA {poly(lactic acid)} or PGA {poly(glycolic acid)}.

In the method for producing the stem cell-nano anticancer drug complex, the stem cell surface antigen may be CD90, CD73 or CD105, and the weight ratio of the nanoparticles to the anticancer compound may be 1:1 to 1:3.

In the above-mentioned method for producing a stem cell-nano anticancer drug complex, the anticancer compound may be doxorubicin, paclitaxel, ABT 737, 5-fluorouracil, BCNU, CCNU, 6-mercaptopurine, nitrogen mustard, cyclophosphamide, Vincristine, vinblastine, cisplatin, methotrexate, cytarabine, thiotepa, busulfan, or procarbazine, and the stem cell may be adipose stem cell, umbilical cord stem cell, induced pluripotent stem cell, or mesenchymal stem cell (MSC).

In the method for producing a stem cell-nano anticancer drug complex, the functional fragment of the antibody may be Fab, F(ab')$_2$, Fab', scFv, Fv, V$_H$H (variable domain of camelid heavy chain) sdAb, diabody or triabody, and the above antibody analogue may be Affibody, Affilin, Affitin, Anticalin, Avimer, DARPin, Fynomer, monobody, VLR (variable lymphocyte receptor), VHH (variable domain of camelid antibody heavy chain), or repebody.

In the case of existing nano anticancer drugs, biodegradable polymers that have been used in formulations are limited with respect to delivering anticancer drugs to target sites due to anticancer drugs being easily dissociated from nanomaterials under acidic pH and blood conditions. Existing nondestructive nanoparticles such as silica, magnetic particles, and carbon-based nanoparticles are not verified with respect to the anticancer drug dosage at which toxicity is overcome, and have problems that must be overcome, such as accumulation in reticular endothelial system (RES) organs. Carbon nanotube-based anticancer drugs are being studied to maximize the effectiveness of such conventional anticancer drugs, and carbon nanotubes (CNTs), which are composed of materials formed on the basis of carbon, such as graphite, carbon tube, fullerene, graphene, and diamond and the like, has been applied in various biomedical fields, including imaging, cancer treatment, etc., due to the mechanical, visual and chemical properties thereof (Bae, S. et al., *Nat. Nanotechnol.* 5, 574, 2010). Recently, carbon nanotubes have been widely used and developed in the biotechnology field as an anticancer drug delivery body, medical image Agent, DNA conjugate, biosensor, biochip, etc., due to the properties of having the largest surface area relative to weight and concentration, and easily binding to biomaterials (Yang, W. et al., *Nanotechnol.*, 18, 412-421, 2007).

Also, gold (Au), which occupies less than 1% of the materials constituting the Earth's crust, is well known as one of the earliest metals used by humankind, and has been used for a long time for gold coins, decoration, and dentistry, as well as for special uses such as fine wires, plating, electrical contacts etc. in electronic equipment, satellites, the nuclear power plant industry etc. Gold is used in the form of various alloys and is manufactured as nanoparticles through various methods. Methods for producing gold nanoparticles include chemical synthesis methods, mechanical production methods, and electrical production methods. In the mechanical production method of pulverizing by utilizing mechanical force, it is difficult to synthesize highly pure particles due to the introduction of impurities, and it is impossible to form uniform nano-sized particles. In practice, methods such as a laser ablation method, an oven beam method, a high energy ball milling method and the like are used. The laser ablation method, which produces nanoparticles by condensing atoms or molecular vapor generated by applying a laser beam on a raw material, is relatively expensive and uses a laser with a low thermal efficiency, and thus has a problem in which the production cost is too high compared to the production yield. The oven beam method of manufacturing nanoparticles by condensing vapor generated by melting substances with low boiling points under a vacuum, and high energy ball milling, which produces nanoparticles by mechanical grinding require highly advanced technology, involve difficult manufacturing processes, and require expensive manufacturing equipment. Also, in the case of the electrical manufacturing method by electrolysis, there is a disadvantage in that the manufacturing time is long, the concentration is low, and the efficiency is low. The chemical synthesis method largely consists of vapor phase methods and liquid phase methods (colloid method), but in the vapor phase method using plasma or a gas evaporation method, expensive equipment is required, and the process is complicated and inefficient, and thus the liquid phase method, which can synthesize uniform particles at low cost and using a simple manufacturing process, is mainly used due to the disadvantages of the vapor phase method. The method for producing gold nanoparticles by the liquid phase method includes a method for producing gold nanoparticles in the form of a hydrosol using a reducing agent or a surfactant after dissociating the compound in a liquid state. Recently, there has been active research and development conducted on producing gold nanoparticles through a liquid reduction method, in which an inorganic compound in the form of a chloroauric acid ($HAuCl_4$) salt is synthesized in a colloidal state using a reducing agent, and loading an anticancer drug thereon to produce anticancer drug complexes with enhanced targeting ability towards cancer cells.

The present inventors, as a result of working to overcome the targeting limitations of conventional nano anticancer drugs and maximize the effectiveness of anticancer drugs, developed a stem cell-nano anticancer drug complex having the homing and apoptosis of stem cells, in which carbon nanotube (CNT) and gold (Au) nanoparticles loaded with anticancer drugs having verified anticancer effects are disposed on the surface of a mesenchymal stem cell (MSC) (FIG. 1).

Hereinafter, the present invention will be described in detail through examples. However, the present invention is not limited to the embodiments disclosed below but can be implemented in a variety of different forms. The following examples make the disclosure of the present invention more complete, and are provided to completely communicate the scope of the invention to a person skilled in the art.

Example 1: Production of Carbon Nanotubes (mwCNT)

Carbon nanotubes to be used in the production of a stem cell-nano anticancer drug complex in which a nano anticancer drug is loaded on the surface of a mesenchymal stem cell (MSC) having a very high targeting ability to cancer cells were produced according to an embodiment of the present invention.

Specifically, as carbon nanotubes have the property of being easily agglomerated by van der Waals attraction and have the problem of being difficult to disperse, acid was used to oxidize carbon atoms at the ends and in defect sites of the carbon nanotubes. A functional group such as a carboxylic group can be introduced by oxidizing a functional group containing oxygen on the surface of the carbon nanotube using an acidic solvent. Carbon nanotubes having carboxyl groups introduced on their surfaces and surface functionalized as described above were prepared as follows. The method of introducing carboxyl groups to the surfaces of the multiwalled carbon nanotubes includes (a) mixing carbon nanotubes in a strong acid solvent to chemically oxidize oxygen-containing functional groups on the surface of the carbon nanotubes, and (b) sonicating the carbon nanotubes in the acid solvent. 20 mg of an SES research product (lot NT-0140, catalog #900-1260, SES Research, Inc., USA) having a diameter in the range of 10 to 30 nm was dissolved in 9 mL of $H_2SO_4$ (98%) 3 mL of $HNO_3$ (65%) at a volume ratio of 3:1 and then sonicated for 30 minutes. Here, the ultrasonic treatment was carried out in the frequency range of 20 to 25 KHz for 80 minutes to 120 minutes. The frequency range may be 20 to 22 KHz, in which case sonication may be carried out for 90 minutes to 110 minutes. By such a process, the agglomerated nanotube structure was cut into a bundle structure of short length, and the shockwaves generated during ultrasonic treatment further dispersed the suspended solid particles. Thereafter, the solution was stirred with a magnetic bar at a rate of 300 rpm while applying heat to the solution at 50° C. for 24 hours. The step for reacting with the acid solvent and the ultrasonic treatment step were repeated once. The MWCNT (MWCNT-COOH) chemically functionalized via the above steps was filtered using a 10 μm diameter filter membrane (Millipore, lot: ROBA 95509), and the filter membrane was then dried under vacuum at 60° C. for 16 to 20 hours. Thereafter, the chemically functionalized MWCNT-COOH was scraped from the filter membrane using a medical scrape made of a stainless steel material. Carboxyl residue (—COOH) was generated at the defect sites on the surface of the nanotube through the experimental steps. The modification of carboxylating the defect sites of the carbon nanotubes increased the solubility of the carbon nanotubes in water or organic solvents.

Example 2: Preparation of Gold Nanoparticles (AuNP)

Gold (Au) nanoparticles to be used in the production of a stem cell-nano anticancer drug complex in which a nano anticancer drug is loaded on the surface of a mesenchymal stem cell (MSC) having a very high targeting ability to cancer cells were produced according to an embodiment of the present invention.

Specifically, in the synthesis of gold nanoparticles, an inorganic compound in a chloroauric acid ($HAuCl_4$) salt state was synthesized in a colloidal state using a reducing agent (utilizing the Turkevich method). After heating 300 mL of 2.2 mM sodium citrate (Sigma Aldrich catalog #S4614) to 100° C., and then adding 2 mL of 25 mM of chloroaurate (Sigma Aldrich catalog #520918), the gold nanoparticles were reduced at 300 RPM. During the above reduction reaction, the solution turned from a transparent color to gray and then red, and the gold nanoparticles synthesized after carrying out the reaction for 15 minutes or less was cooled at room temperature for at least 30 minutes at room temperature and thereby stabilized. All of the above reaction was carried out using tertiary distilled water as a solvent. The synthesized gold nanoparticles are in an equilibrium state due to citrate ions, but have the property of losing their equilibrium state by salt or lyophilization and being easily agglomerated by the van der Waals attraction between particles. To compensate for these drawbacks, 1 mg/mL of a polymer (α-Mercapto-ω-carboxy-PEG) was reacted with 2 mg/mL of gold nanoparticles for 24 hours to obtain a self-assembled monolayer on the surface of the gold nanoparticles to improve steric stability, and electrostatic safety was also improved due to the carboxylate negative charge of the polymer. The polymer-coated carboxylated gold nanoparticles (AuNP-COOH) thus prepared were separated from the solvent at a rate of 16000 g using a centrifugal separator and re-suspended with tertiary distilled water, and then used as a suspension.

Example 3: EDC Linker Connection

In accordance with an embodiment of the present invention, an EDC linker was bound to the carbon nanotubes prepared in Example 1 and the gold nanoparticles prepared in Example 2 to ensure the stability of protein binding.

Specifically, the reaction binding the EDC linker to the carbon nanotube (MWCNT-COOH) and the gold nanoparticle (AuNP-COOH) is carried out in weakly acidic 2-morpholinoethanesulfonic acid, and an MES buffer (low moisture content≥99%, Sigma-Aldrich CAT: M 3671) was used to adjust the pH of the solution. First, 10 mg of AuNP-COOH and 3.2 mg of MWCNT-COOH were placed in 1.6 kg of the MES buffer (50 mM, pH 5.5), and then a tip sonicator (company: Misonix sonicators, Product: sonicator 4000) was used to disperse for 5 minutes using a 3 seconds on/3 seconds off cycle. Thereafter, a solution prepared by mixing 1.6 mL of NHS (400 mM) (N-hydroxysuccinimide, Cas: 06066-82-6) in the MES buffer (50 mM, pH 5.5) was added to the ultrasonically pulverized solution, and then mixed for 30 minutes using a Rocker. Thereafter, 10 mL of EDC solution (20 mM) (N-(3-dimethylaminopropyl)-N-ethylcarbodiimide hydrochloride; Sigma, Lot No .: 040 M 17411 V) was added to the sonicated solution and mixed for 30 minutes with a Rocker to produce EDC linker-connected carbon nanotubes (EDC-MWCNT-COOH) and gold nanoparticles (EDC-AuNP-COOH).

The above mixture was placed in a 4 Centricon YM-50 filter tube (Amicon ultra-15, 50K device-50000 NMWL, TM Millpore, USA) and centrifuged at 2,000 rpm, and then washed 3 or more times with an MES buffer (50 mM). Here, centrifugation was carried out for 20 minutes at a time. Ultrasonic pulverization was further performed for 5 minutes under 3 seconds on/3 seconds off conditions on 5 mg of the MWCNT-COOH in 5 mL of PBS (phosphate buffered saline) using a tip sonicator, and this state was used as a control group for a carbon nanotube-based anticancer drug, described below, loaded with anticancer drugs.

Example 4: Production of Carbon Nanotube-Based Anticancer Drug 4-1: Production of mwCNT with Anticancer Drug Loaded by Covalent Bond The carbon nanotube-based anticancer drug according to an embodiment of the present invention increased the binding ratio of anticancer drugs compared with the conventional anticancer drug using covalent bonding. In order to increase the binding ratio of the anticancer drug relative to conventional techniques, the pH at the time of binding of the EDC linker bond and the anticancer drug was adjusted. In the pH range of 4-6 at which the EDC linker is most easily attached, maximal binding of the EDC linker was induced by selecting a pH of 5.5, and when binding the anticancer drug the pH was raised to 6, which, although not satisfying the pH range of 7-8, which is the condition for maximum loading of the anticancer drug, is in the pH range at which EDC hydrolysis can be suppressed. The two changes in pH (pH 5.5 and 6) induced strong covalent binding by stably maintaining the EDC linker bond while maximizing the loading of the anticancer drug.

Thereafter, the prepared EDC-mwCNT solution was bound with doxorubicin (Doxorubicin, DOX, Sigma-Aldrich, Cat #D1515), which is a cancer cell nuclear division inhibiting anticancer drug. Here, EDC-mwCNT and the anticancer drug were mixed at a concentration ratio of 1:1 and stirred with a platform shaker for 14 to 18 hours at 4° C., and then the EDC-mwCNT solution loaded with the anticancer drug was centrifuged at 2,000 rpm using a Centricon YM-50 filter tube, and the remaining unbound doxorubicin was removed by removing the supernatant. Next, mwCNT (mwCNT-DOX) loaded with doxorubicin was dissolved in 5 mL of PBS and used in the following experiment.

4-2: Production of AuNP with Anticancer Drug Loaded by Covalent Bond

The gold nanoparticle-based anticancer drug according to an embodiment of the present invention was bound using an EDC/NHS cross-linked chemical. By using the MES buffer, which is convenient for stabilizing pH, as a solvent, a stable binding reaction between gold nanoparticles and an anticancer drug was induced, and an NHS-ester derivative was formed on the surface of the particles by carrying out the reaction at a pH of 6 at which the hydrolysis efficiency of EDC can be reduced.

Specifically, the prepared AuNP-NHS ester solution was bound with doxorubicin (Doxorubicin, DOX, Sigma-Aldrich, Cat #D1515) which is a cancer cell nuclear division suppression anticancer drug. Here, AuNP-NHS ester having a concentration of 4 nM and an anticancer drug having a concentration of 0.17 mM were mixed and stirred at 4° C. for 20 to 24 hours using a magnetic stirrer, The AuNP-NHS ester solution loaded with the anticancer drug was centrifuged at 10,000 g using a centrifugal separator, and the supernatant was removed to remove residual unbound doxorubicin. Next, AuNP (AuNP-DOX) loaded with doxorubicin was dissolved in 1 mL of PBS and used for the following experiment.

Example 5: Binding of MSC-Nano Anticancer Drug

Figure 2:
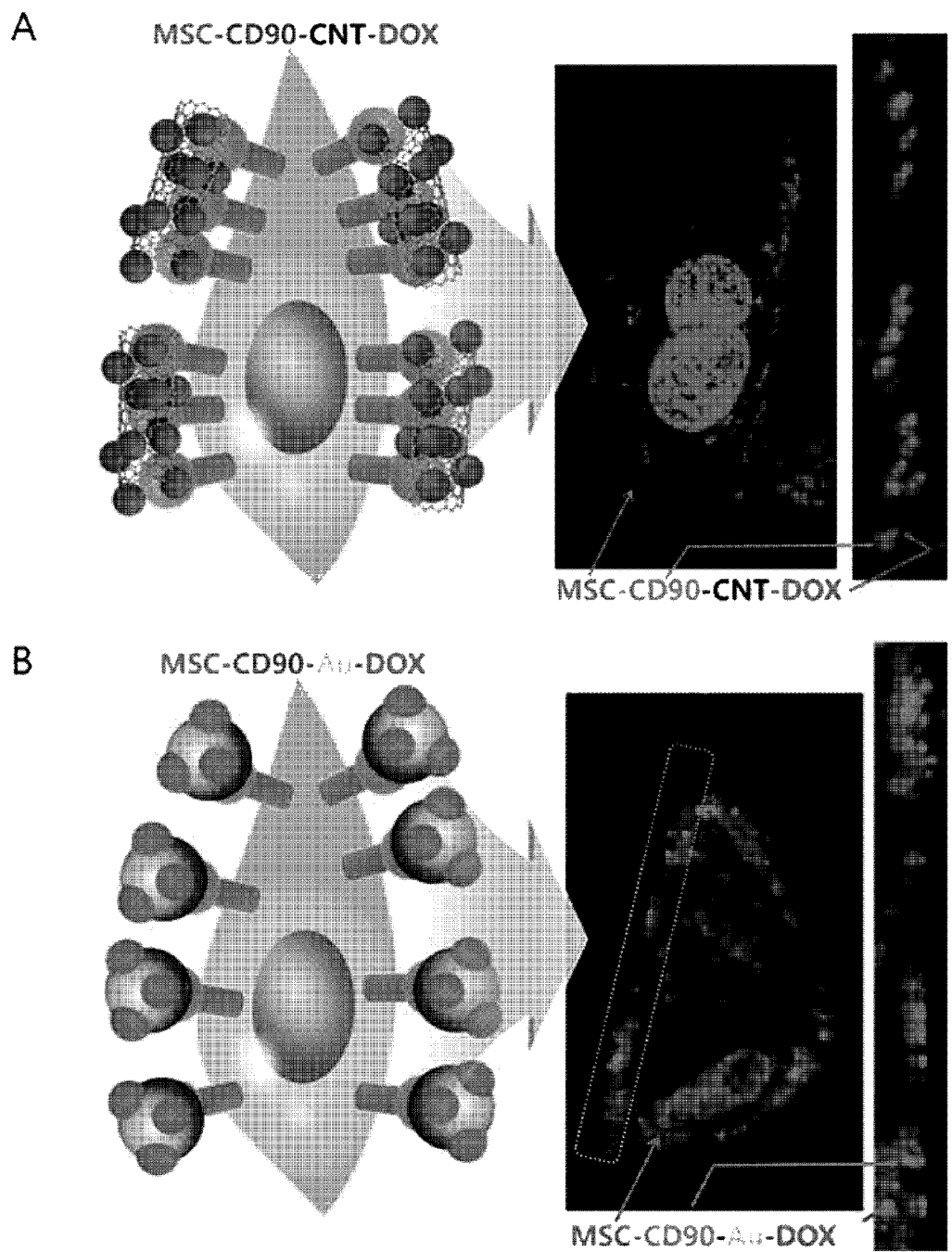
FIG. 2 includes a set of a diagram and a microscope image for confirming that doxorubicin-bound mwCNT and Au are appropriately attached to a stem cell surface, using a confocal microscope after preparing (A) a stem cell-carbon nanotube-based nano anticancer drug complex (hMSC-CD90-mwCNT-DOX) and (B) a stem cell-gold nanoparticle-based nano anticancer drug complex (hMSC-CD90-Au-DOX) which are prepared in accordance with an exemplary embodiment.

According to an embodiment of the present invention, an antibody specifically recognizing CD90, which is a marker protein, was reacted on the surface of MSC, which exhibits non-target and non-toxicity with respect to surrounding normal cells, but for which tracking ability and apoptosis ability are confirmed with respect to non-small cell lung cancer and small cell lung cancer, at a concentration of 20 μg/ml with EDC-mwCNT prepared in Example 3 and AuNP-NHS ester solution, and then doxorubicin was bound and stirring was performed with a platform shaker at 4° C. for 14-18 hours. Subsequently, the EDC-mwCNT and AuNP-NHS ester solutions loaded with anticancer drugs were centrifuged at 4,000 rpm using a Centricon YM-50 filter tube, and the remaining unbound doxorubicin and antibodies were removed by removing the supernatant. The CD90 antibody-doxorubicin-mwCNT complex (CD90-mwCNT-DOX) and the CD90 antibody-doxorubicin-AuNP complex (CD90-AuNP-DOX) prepared in Example 3 were reacted with stem cells at a concentration of 1 μg/mL, after which unbound CD90-mwCNT-DOX and CD90-AuNP-DOX were removed, and the DOX fluorescence wavelength of the bound stem cell-nano anticancer drug complex (hMSC) was measured using a fluorescence microplate reader (VICTOR X3, PerkinElmer)-CD90-mwCNT-DOX, hMSC-CD90-AuNP-DOX). In the case of hMSC-CD90-mwCNT-DOX, a stem cell-nano anticancer drug complex (hMSC-CD90-mwCNT-DOX) loaded with 72 ng/mL of doxorubicin nano anticancer drug per 1×10$^5$ stem cells was prepared, and a focused fluorescence microscope was used to confirm that doxorubicin-conjugated mwCNT and AuNP were correctly attached to the surface of stem cells (FIG. 2).

Example 6: Confirmation of Optimization of Binding of Nano Anticancer Drugs of Stem Cells According to an embodiment of the present invention, the degree of anticancer drug loading per cell, the change in the degree of anticancer drug loading per cell according to CD antibody, the anticancer drug duration according to time of hMSC-CD90-mwCNT-DOX, and the change in cell viability of stem cells following nano anticancer drug binding by time frame were confirmed for a stem cell-nano anticancer drug complex (hMSC-CD90-mwCNT-DOX, hMSC-CD73-mwCNT-DOX).

Figure 3:
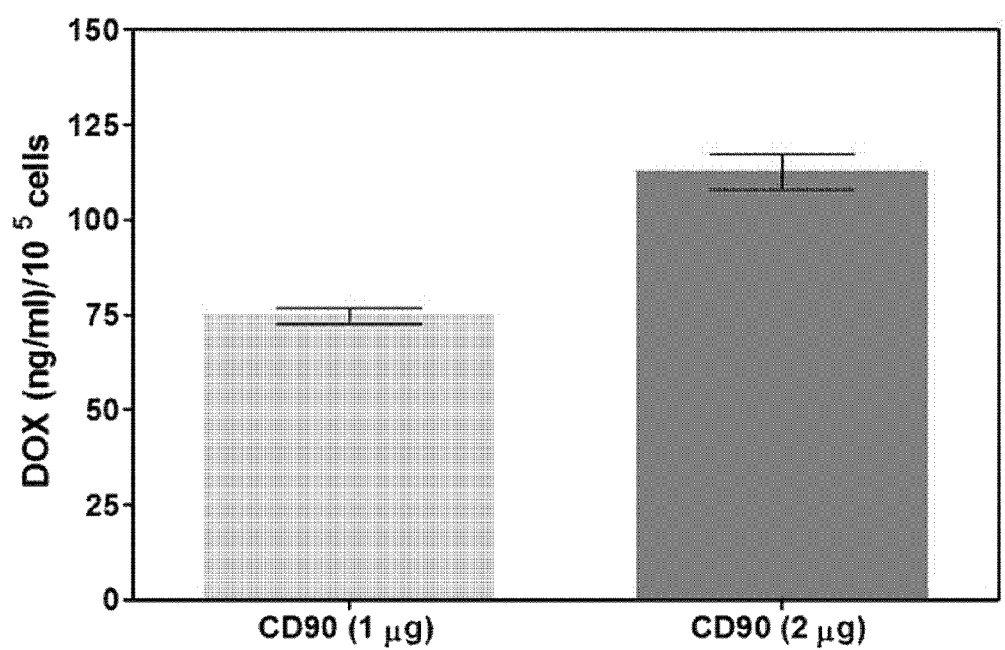
FIG. 3 is a graph for analyzing a degree of anticancer drug loading per cell of a stem cell-nano anticancer drug complex (hMSC-CD90-mCNT-DOX) which is bound using an antibody bound to stem cell marker protein CD90.
Figure 4:
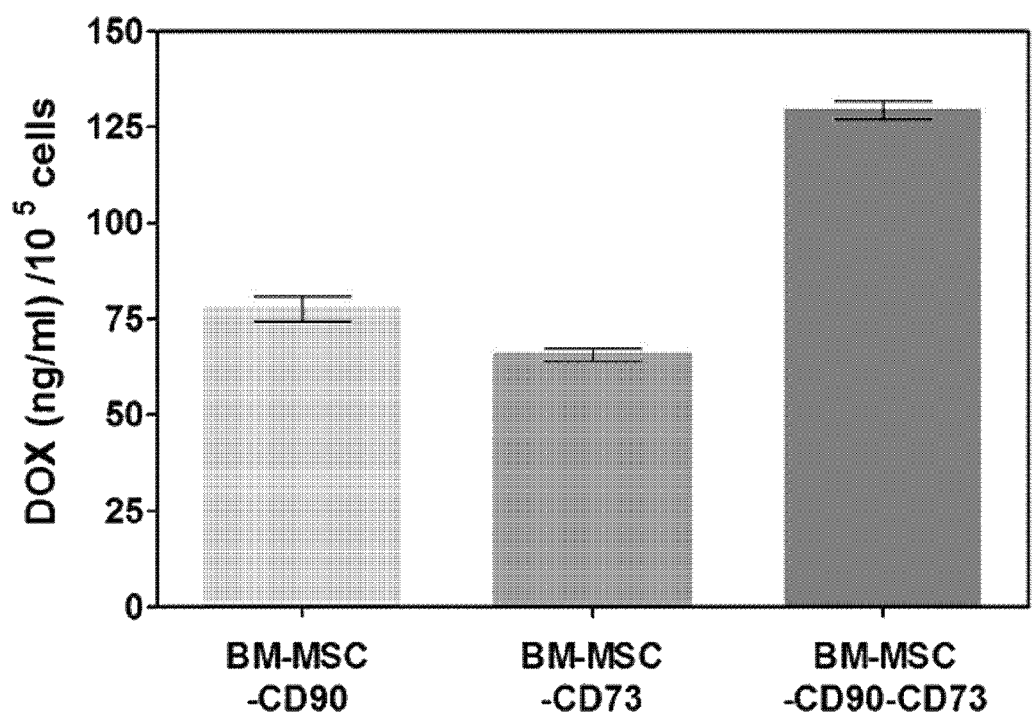
FIG. 4 is a graph for analyzing a difference of a loading degree per cell of a stem cell-nano anticancer drug complex (hMSC-CD90-mwCNT-DOX, hMSC-CD73-mwCNT-DOX) bound using an antibody which is bound with stem cell target protein CD90 or CD73.

Specifically, in order to confirm the loading degree of doxorubicin according to the concentration of MSC marker protein and nano anticancer drug, CD90-mwCNT-DOX was treated with MS90 at each concentration (1, 2 μg/ml) for 2 hours in MSC. After washing three times with 1× PBS, the amount of bound nano doxorubicin anticancer drug was measured using a fluorescence microplate reader (FIG. 3). Moreover, stem cell-nano anticancer drug complexes (CD90-mwCNT-DOX, CD73-mwCNT-DOX, CD90-CD73-mwCNT-DOX) bound to each of the CD antibodies were treated for 2 hours at a concentration of 1 μg/ml in MSC and washed with 1× PBS, and then the fluorescence wavelength of the nano doxorubicin anticancer drug bound to MSC was measured using a fluorescent microplate reader to determine the change in the amount of bound doxorubicin anticancer per cell according to the bound CD antibody (FIG. 4). Also, after binding mwCNT-CD90-DOX to MSC to determine how much nano anticancer drug bound to MSC was retained, the degree of nano-doxorubicin anticancer drug retention was analyzed using flow cytometry (FACS) 24, 48, 72, and 144 hours after binding mwCNT-CD90-DOX to MSC. 5×10$^3$ cells of MSC were seeded in a 96-well plate and cultured for 18 hours, and then, after treating mwCNT-CD90-DOX at various concentrations (1, 2, 5, and 10 μg/ml) for various durations (24, 48, 72, and 144 hours), 100 μL of MTT reagent {3-(4,5-dimethylthiazol-2-yl)-2,5-diphenyltetrarium bromide, 3-(4,5-Dimethylthiazol-2-yl)-2,5-diphenyltetrazolium bromide} having a concentration of 1 mg/mL was added to each well, and cultured at 37° C. for 2 hours. Subsequently, 100 μL of a DMSO solution was added to each well, and the absorbance was measured at 570 nm using a microplate reader (UVM 340, ASYS) to confirm the survival rate of MSC.

Figure 5:
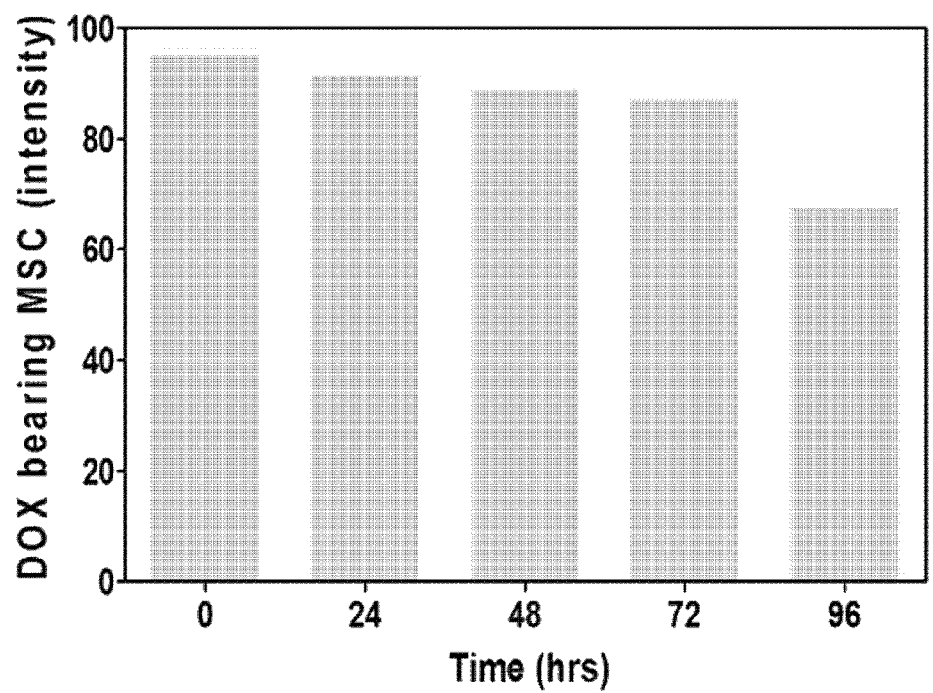
FIG. 5 is a graph for analyzing a degree of an anticancer combination lasting period according to time of stem cell-nano anticancer drug complex (hMSC-CD90-mwCNT-DOX, hMSC-CD73-mwCNT-DOX) using an antibody which is bound to stem cell target protein CD90 or CD73.
Figure 6:
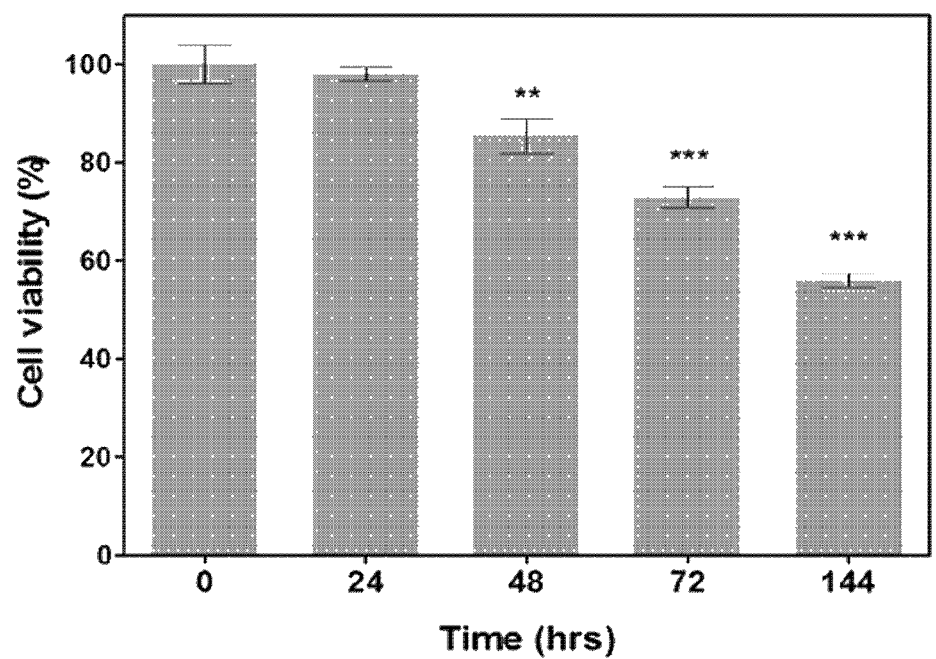
FIG. 6 is a graph for analyzing cell viability differences of stem cells of the stem cell-nano anticancer drug complex (hMSC-CD90-mwCNT-DOX, hMSC-CD73-mwCNT-DOX).

As a result, it was confirmed that binding the two CD90-CD73 antibodies together results in a higher binding of the nano anticancer drugs than when using the CD73 and CD90 antibodies individually, and it was found that the nano anticancer drug was maintained high 96 hours after mwCNT-DOX binding (FIG. 5). In addition, even when 10 μg/mL of mwCNT-CD90-DOX was bound, MSC itself was not toxic, and it was confirmed that the MSC survival rate was maintained at 60% or higher after 144 hours (FIG. 6).

Experimental Example 1: MSC Toxicity Verification by Marker Protein of Stem Cell-Nano Anticancer Drug Complex According to an embodiment of the present invention, the marker protein antibodies capable of binding to stem cells during the production of the stem cell-nano anticancer drug complex include CD90, CD73, and CD105. Stem cell-nano anticancer drug complexes (MSC-CD90-mwCNT-DOX and MSC-CD 73-mwCNT-DOX) manufactured so as to be able to bind to marker protein differently were treated for a short duration (72 hr) and a long duration (240 hr) in lung cancer cells (H1975), and the apoptosis of the stem cell-nano anticancer drug complexes was analyzed.

Specifically, a lung cancer cell line (H1975) was seeded at a ratio of 4×10$^5$ cells per well in a 100 π culture plate and then cultured in DMEM (Dulbecco's Modified Eagle's, FBS) containing 10% fetal bovine serum (FBS) medium. A ratio of 4×10$^5$ cells of the stem cell-nano anticancer drug complex (MSC-CD90-mwCNT-DOX and MSC-CD 73-mwCNT-DOX) prepared so as to be able to bind differently to the marker protein were treated for a short duration (72 hr) and a long duration (240 hr) in lung cancer cells (H1975), and after staining stem cell specific markers (CD90, CD73) and fluorescent cell apoptosis marker (Annexin V), the apoptosis of MSC and changes to other marker proteins were analyzed using FACS.

Figure 7:
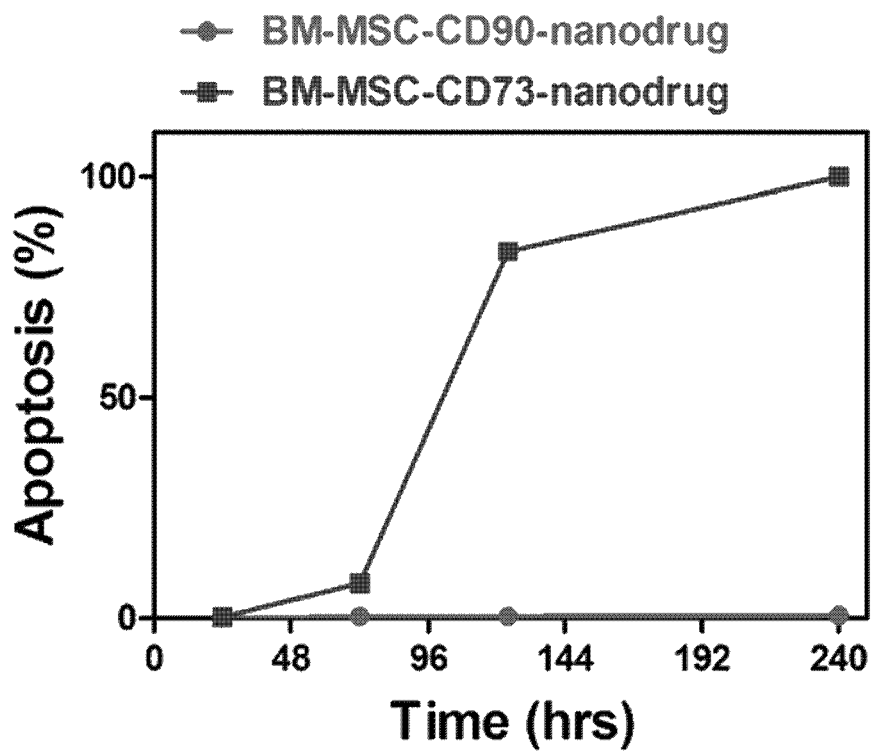
FIG. 7 is a graph for analyzing viability differences of stem cells per time after binding with the stem cell-nano anticancer drug complex (hMSC-CD90-mwCNT-DIX, hMSC-CD73-mwCNT-DOX).

As a result, the MSC-CD90-mwCNT-DOX experimental group showed no toxicity of the MSC itself compared with the MSC-CD 73-mwCNT-DOX experimental group, and the MSC-CD 73-mwCNT-DOX experimental group showed that the stem cells themselves were killed due to the toxicity associated with the increase of ROS. Thus, it was found that the stem cell-nano anticancer drug complex which is the MSC-CD90-mwCNT-DOX experimental group was suitable for the experiment FIG. 7).

Experimental Example 2: Analysis of Changes in MSC Intracellular Calcium Signaling by Marker Proteins of Stem Cell-Nano Anticancer Drug Complex After reacting a stem cell-nano anticancer drug complex (MSC-CD90-mwCNT-DOX and MSC-CD 73-mwCNT-DOX) prepared according to an embodiment of the present invention with lung cancer cells (H1975), intracellular calcium signaling in MSC cells of the stem cell-nano anticancer drug complex was analyzed.

Specifically, lung cancer cells (H1975) and stem cell-nano anticancer drug complexes (MSC-CD90-mwCNT-DOX and MSC-CD73-mwCNT-DOX) were cultured at a ratio of 4×10$^5$ cells for 48 hours on a coverslip, and then 0.05% Pluronic F-127 containing 4 μM of Fura-2 was added to physiological saline and reacted together in the dark for 15 minutes at room temperature. Thereafter, using a fluorescence microscope, the change in MSC intracellular calcium signaling of the stem cell-nano anticancer drug complexes (MSC-CD90-mwCNT-DOX and MSC-CD 73-mwCNT-DOX) according to marker protein was confirmed at excitation/emission fluorescence wavelengths of 340/510 nm, and the change was analyzed using the MetaFluor system.

Figure 8:
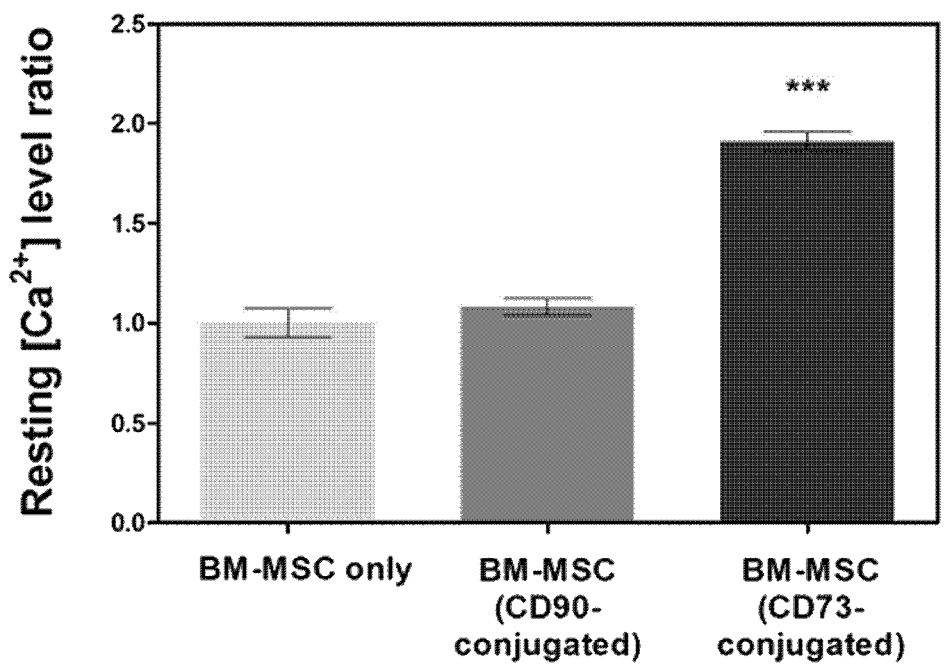
FIG. 8 is a graph showing changes in the intracellular calcium concentration of the stem cell-nano anticancer drug complex (hMSC-CD90-mwCNT-DOX, hMSC-CD 73-mwCNT-DOX).
Figure 9:
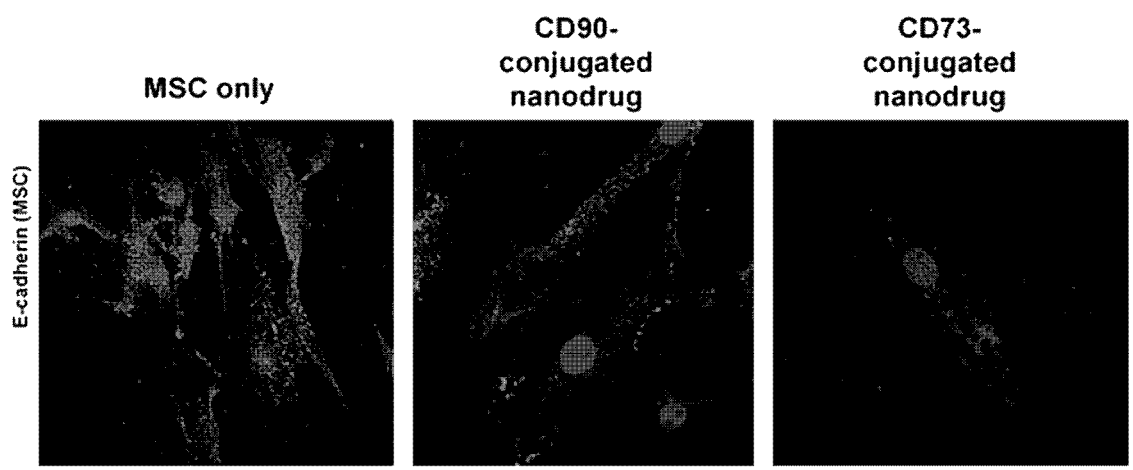
FIG. 9 is a confocal microscopy image confirming MSC cell damage of the stem cell-nano anticancer drug complex (hMSC-CD90-mwCNT-DOX, hMSC-CD73-mwCNT-DOX).

As a result, compared to the experimental group, changes in MSC calcium signaling were found to be highest in the experimental group MSC-CD73-mwCNT-DOX (FIG. 8), and cell damage was found to occur most frequently in experimental group MSC-CD73-mwCNT-DOX (FIG. 9).

Experimental Example 3: Analysis of Cancer Cell Targeting Ability and Functionality of Stem Cell-Nano Anticancer Drug Complex Through analysis of changes in the cancer cell targeting ability after preparation of the stem cell-nano anticancer drug complex (hMSC-CD90-mwCNT-DOX) prepared according to an embodiment of the present invention, the functionality of the stem cell-nano anticancer drug complex was confirmed.

Specifically, the experimental cell line used NHFB (human fibroblast, normal cell line), A549 (non-small cell lung cancer strain), MDA-MB-231 (breast cancer cell line) and U87 MG (Shingyeonggyeo celloma). Analysis of migration for sorting was performed in a 24 well transwell using a polycarbonate membrane with 8 μm porosity. The MSC was placed in the upper chamber attached to the transwell at a density of 200 μl medium (α-minimum essential medium+ 0.5% thick serum) at $5 \times 10^4$ cells/ml. The lower chamber contained 500 μl of the medium in which NHFB (human fibroblast, normal cell line), A549 (non-small cell lung cancer strain), MDA-MB-231 (breast cancer cell line) and U87MG (glioblastoma cell line) were cultured. After culturing at 37° C. under 5% $CO_2$ for 5 hours, the non-migrated cells were removed from the upper surface of the membrane and washed with phosphate buffered saline. Thereafter, the membrane was fixed in 100% methanol for 1 minute and stained for 30 minutes with 1% DAPI (4',6-Diamidino-2-phenylindole, Dihydrochloride) which is a cell nucleus staining reagent. The number of migrating cells was determined by counting ten random parts per well under a ×200 magnification microscope, and for comparison, stem cell-nano anticancer drug complex (MSC-CD90-CD73-CNT-DOX) bound together with CD90, CD73 antibody and stem cells uptaken with nano anticancer drugs were also analyzed.

Figure 10:
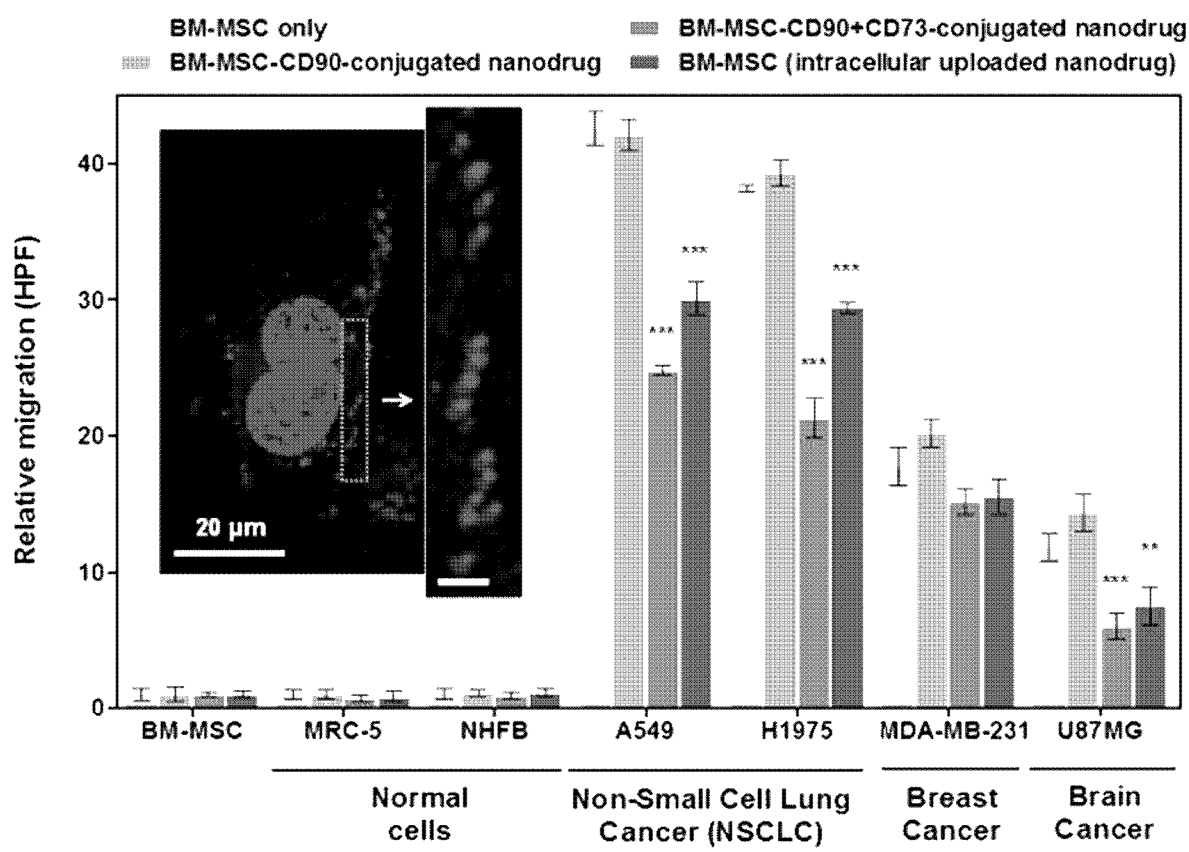
FIG. 10 is a graph of analyzing the functionality of the stem cell-nano anticancer drug complex by analyzing cancer cell target ability differences after the preparation of the stem cell-nano anticancer drug complex (hMSC-CD90-mwCNT-DOX) of the present invention, after combining with a confocal microscopy image which confirms the nano anticancer drug bound to a cell surface.

As a result, the cancer targeting ability was found to be similar to pure MSC even after preparing the stem cell-nano anticancer drug complex (hMSC-CD90-mwCNT-DOX) (FIG. 10).

Experimental Example 4: Nano Anticancer Drug Loading Experimental Group in Stem Cells and Stem Cell-Nano Anticancer Drug Complex Efficiency of Nano Anticancer Drug and Lung Cancer Target Function Comparison Changes in doxorubicin antitumor agent loading efficiency and lung cancer cell targeting ability of stem cell-nano anticancer drug complex prepared according to an embodiment of the present invention were analyzed through comparison with experimental group in which nano anticancer drug is loaded in stem cells.

Specifically, the lung cancer cells (H1975) and the stem cell-nano anticancer drug complexes (MSC-CD90-mwCNT-DOX and MSC-CD73-mwCNT-DOX) were cultured at a ratio of $4 \times 10^5$ cells for 48 hours on a coverslip, and then 0.05% Pluronic F-127 containing 4 μM of Fura-2 was added to physiological saline and reacted together for 15 minutes in the dark at room temperature. Thereafter, using a fluorescence microscope, the change in MSC intracellular calcium signaling of the stem cell-nano anticancer drug complexes (MSC-CD90-mwCNT-DOX and MSC-CD 73 (TMC)) according to marker protein was confirmed at excitation/emission fluorescence wavelengths of 340/510 nm, and changes were analyzed using the MetaFluor system.

Figure 11:
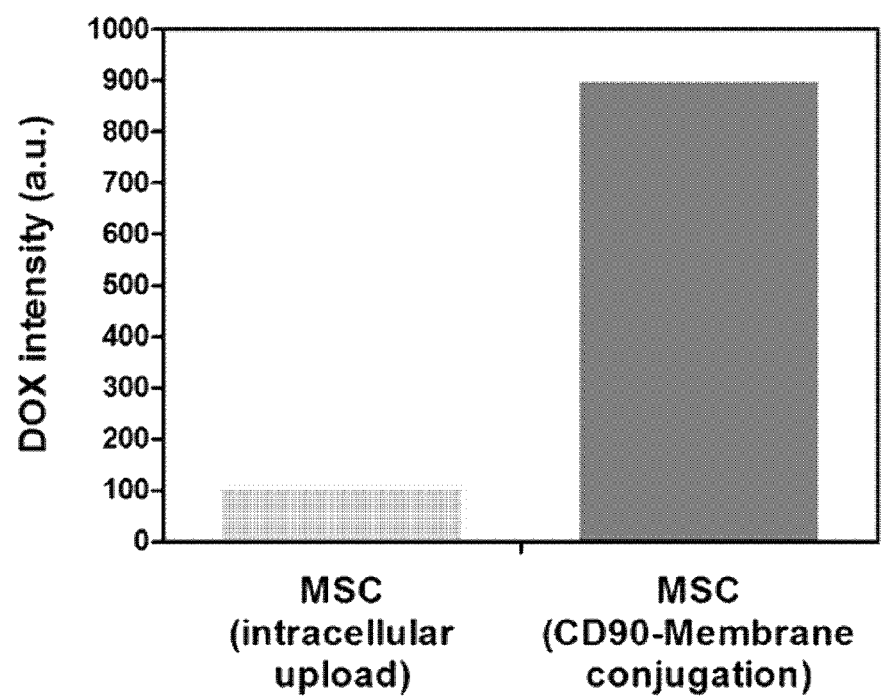
FIG. 11 is a graph analyzing the concentration of a doxorubicin anticancer drug in a stem cell-nano anticancer drug complex loaded with a nano anticancer drug in a stem cell or bound to a membrane protein of a stem cell.
Figure 12:
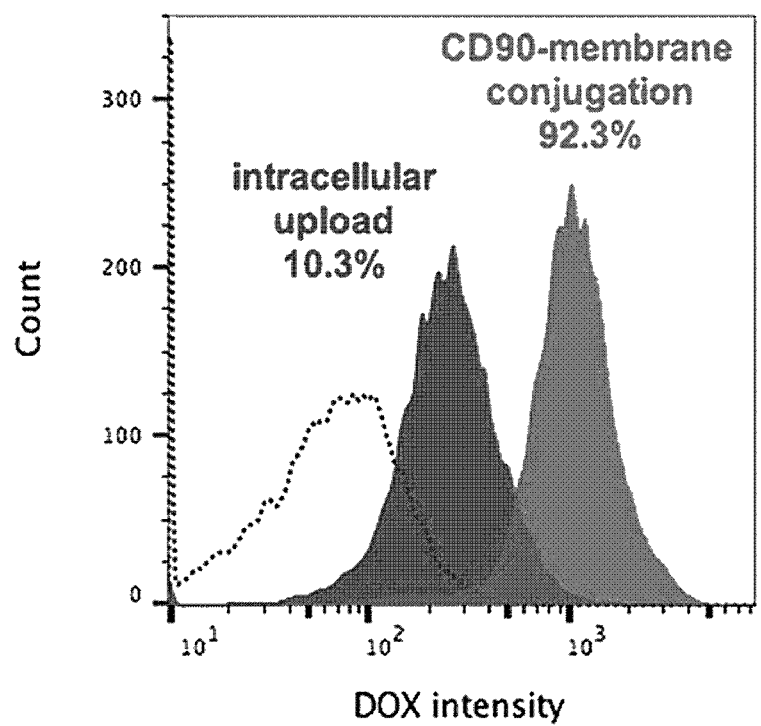
FIG. 12 is a graph analyzing the loading amount of the doxorubicin anticancer drug in the stem cell-nano anticancer drug complex of the present invention.
Figure 13:
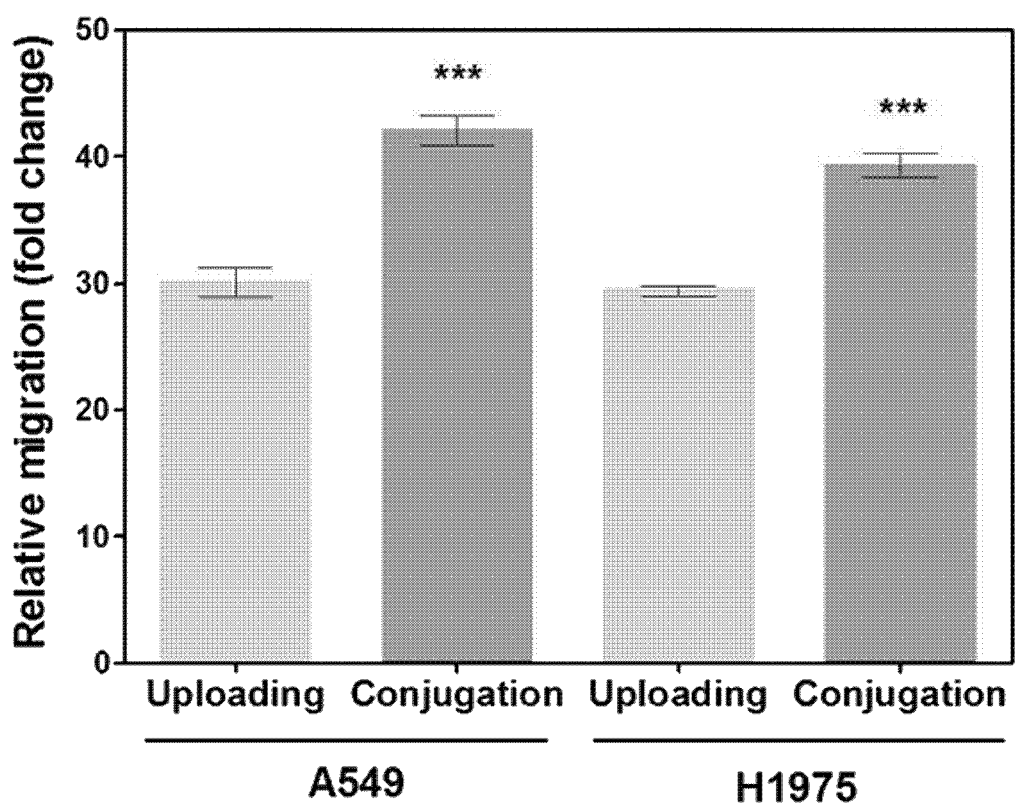
FIG. 13 is a graph of target capability analysis of the non-small cell lung cancer cell lines (A549 and H1975) of the stem cell-nano anticancer drug complex of the present invention.

As a result, doxorubicin antitumor agent loading efficiency (FIGS. 11 and 12) and lung cancer targeting ability of the stem cell-nano anticancer drug complex (hMSC-CD90-mwCNT-DOX) were found to be superior compared to the experimental group in which nano anticancer drug is loaded in stem cells (FIG. 13).

Experimental Example 5: Verification of Apoptosis of MSC After Preparation of Stem Cell-Nano Anticancer Drug Complex According to an embodiment of the present invention, the inherent toxicity of the MSC stem cells was analyzed, in comparison with the stem cell group loaded with the nano anticancer drug, after producing the stem cell-nano anticancer drug complex with optimized functionality.

Specifically, after adsorbing or conjugating the nano anticancer drug at a concentration of 1 μg/ml for 2 hours in $5 \times 10^5$ MSC cells and then replacing the medium, the degree of apoptosis of the stem cells was analyzed using FACS while culturing the nano anticancer drug for up to 24 hours with lung cancer cells after staining the stem cells with stem cell specific marker (CD90) and fluorescent apoptosis marker (Annexin V).

Figure 14:
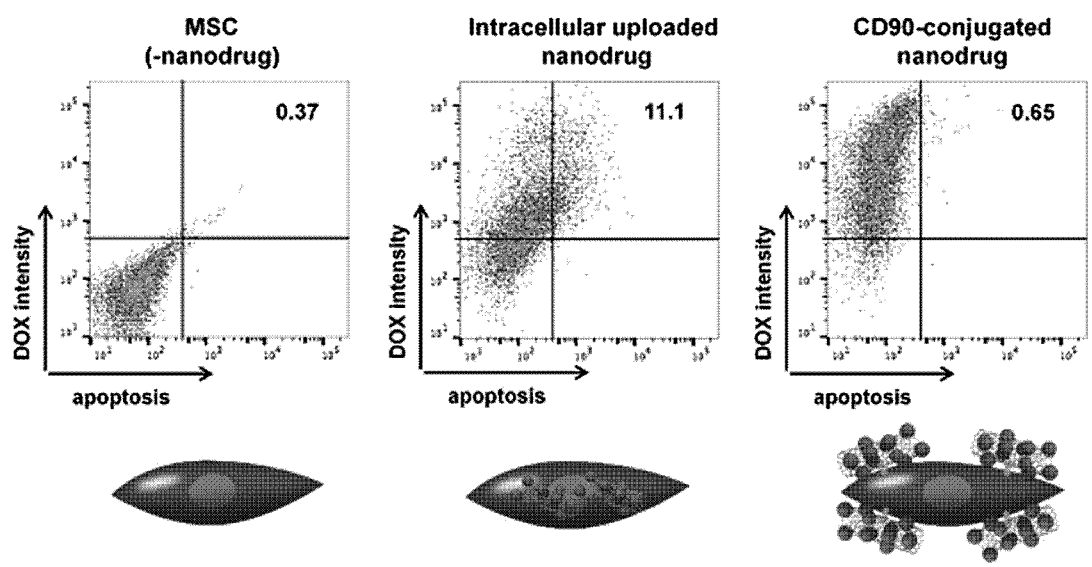
FIG. 14 is a graph comparatively analyzing the unique toxicity between an MSC intracellular CNT-DOX uploading experimental group and MSC conjugation CNT-DOX experimental group stem cells.

As a result, it was confirmed that the MSC toxicity is low in the experimental group of the stem cell-nano anticancer drug complex compared with the experimental group in which nano anticancer drug is loaded in stem cells (FIG. 14).

Experimental Example 6: Verification of Amplified Cancer Cell Apoptosis Ability of Stem Cell-Nano Anticancer Drug Complex In accordance with an embodiment of the present invention, the function of the stem cell-nano anticancer drug complex optimized for function was injected into cancer cells, and the apoptosis ability was compared and analyzed.

Specifically, in order to analyze whether the stem cell-nano anticancer drug complex of the present invention has amplified apoptosis compared with glass MSC (BM-MSC) and the experimental group in which nano anticancer drug is loaded in the stem cell, a lung cancer cell line (H1975) was seeded in a 100π culture plate at a rate of $5 \times 10^5$ cells per well and then cultured in DMEM (Dulbecco's Modified Eagle's, FBS) containing 10% fetal bovine serum (FBS) medium. Here, the culturing device was maintained in a humid state at a temperature of 37° C. under the condition of 5% $CO_2$. The function-optimized stem cell-nano anticancer drug complex, glass MSC (BM-MSC), and the experimental group in which nano anticancer drug is loaded in stem cells were treated with $5 \times 10^5$ cells and then observed for up to 240 hours. Analysis by flow cytometry (FACS) was performed after staining of lung cancer cells (CD54) and stem cell specific marker (CD90) and fluorescent apoptosis marker (Annexin V).

Figure 15:
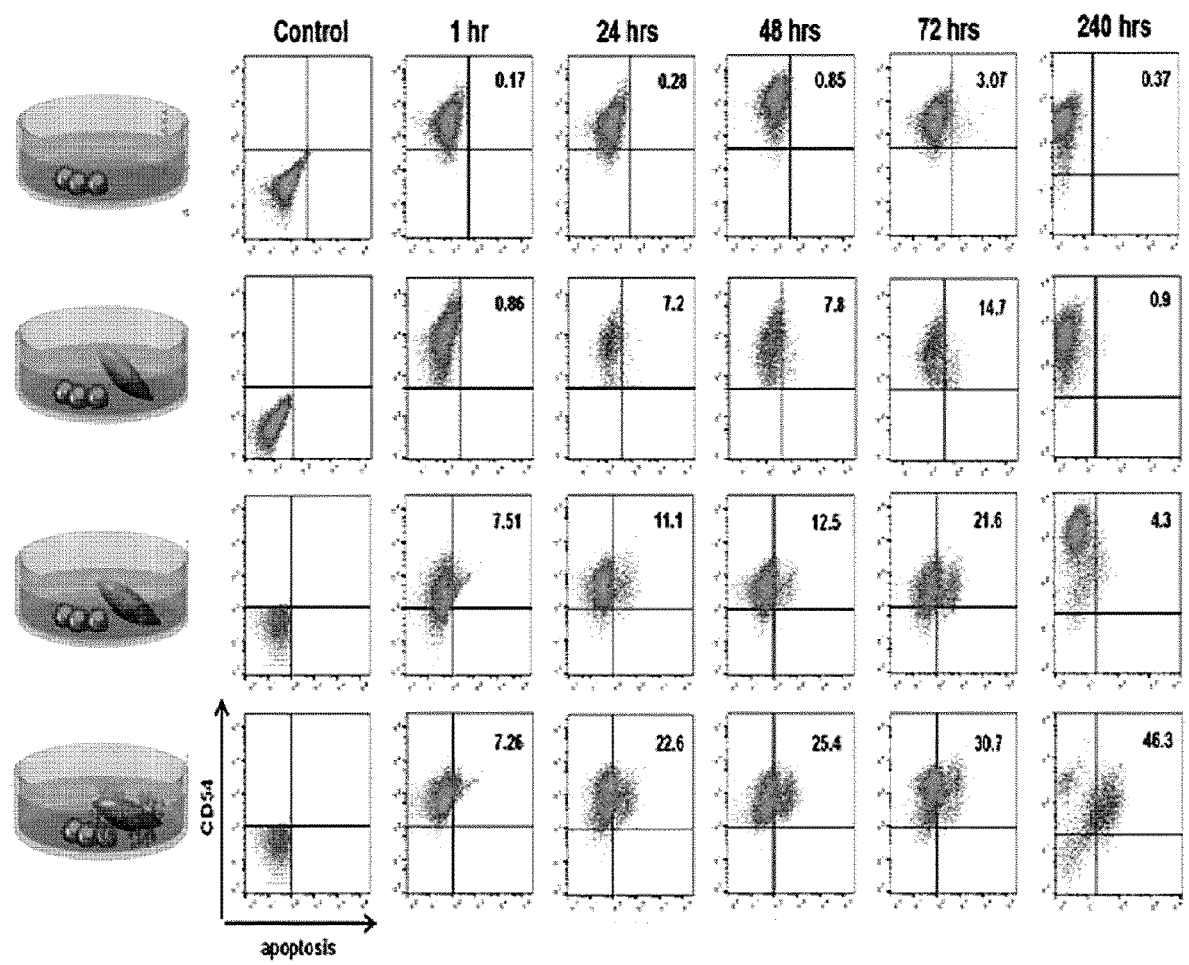
FIG. 15 is a time chart of lung cancer for a long time in an MSC badge treatment group, MSC treatment group, MSC intracellular CNT-DOX uploading experimental group, MSC conjugation CNT-DOX experimental group, and control group according to an exemplary embodiment of the present invention with flow cytometric analysis data obtained by comparative analysis of cell (H1975) death ability.
Figure 16:
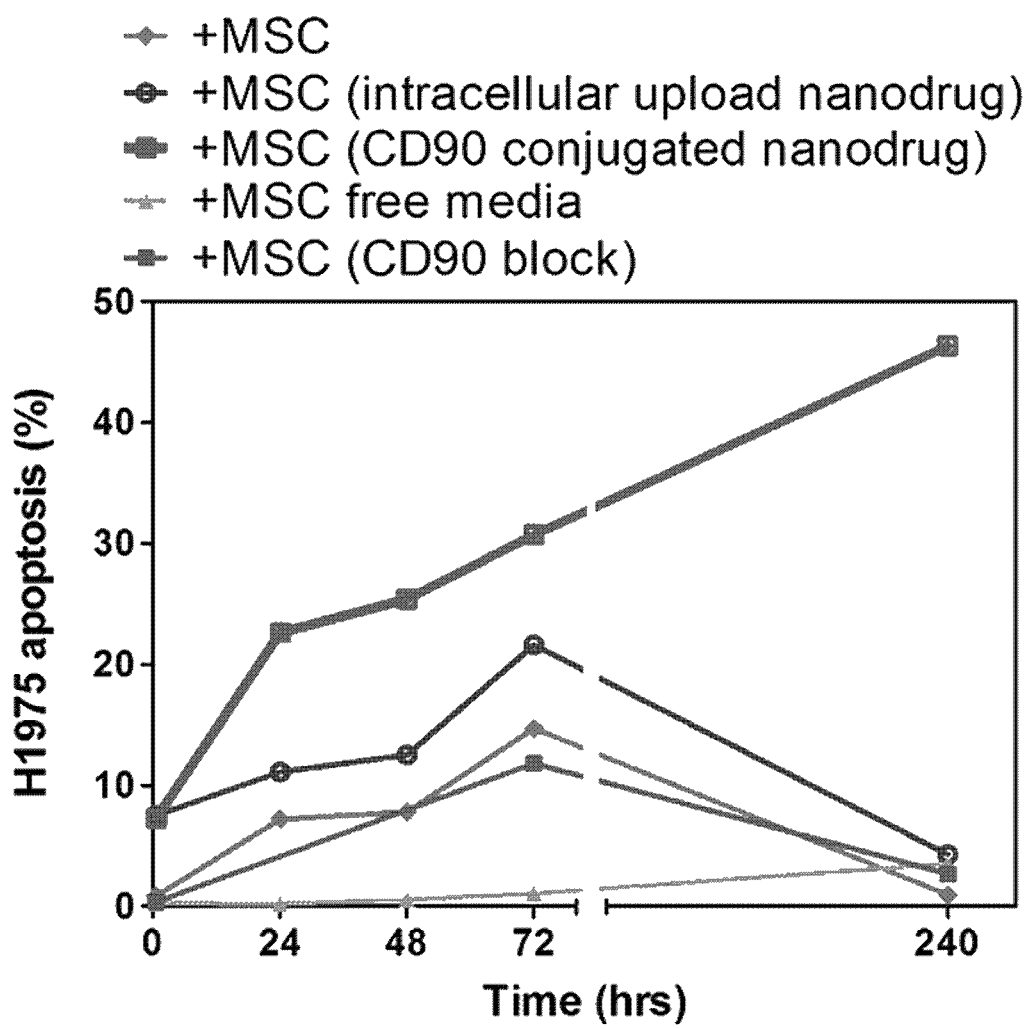
FIG. 16 shows a time course of lung cancer for a long time in the MSC badge treatment group, the MSC treatment group, the MSC intracellular CNT-DOX uploading experimental group, the MSC conjugation CNT-DOX experimental group and the control group according to an embodiment of the present invention (H1975) apoptosis ability of the cells.
Figure 17:
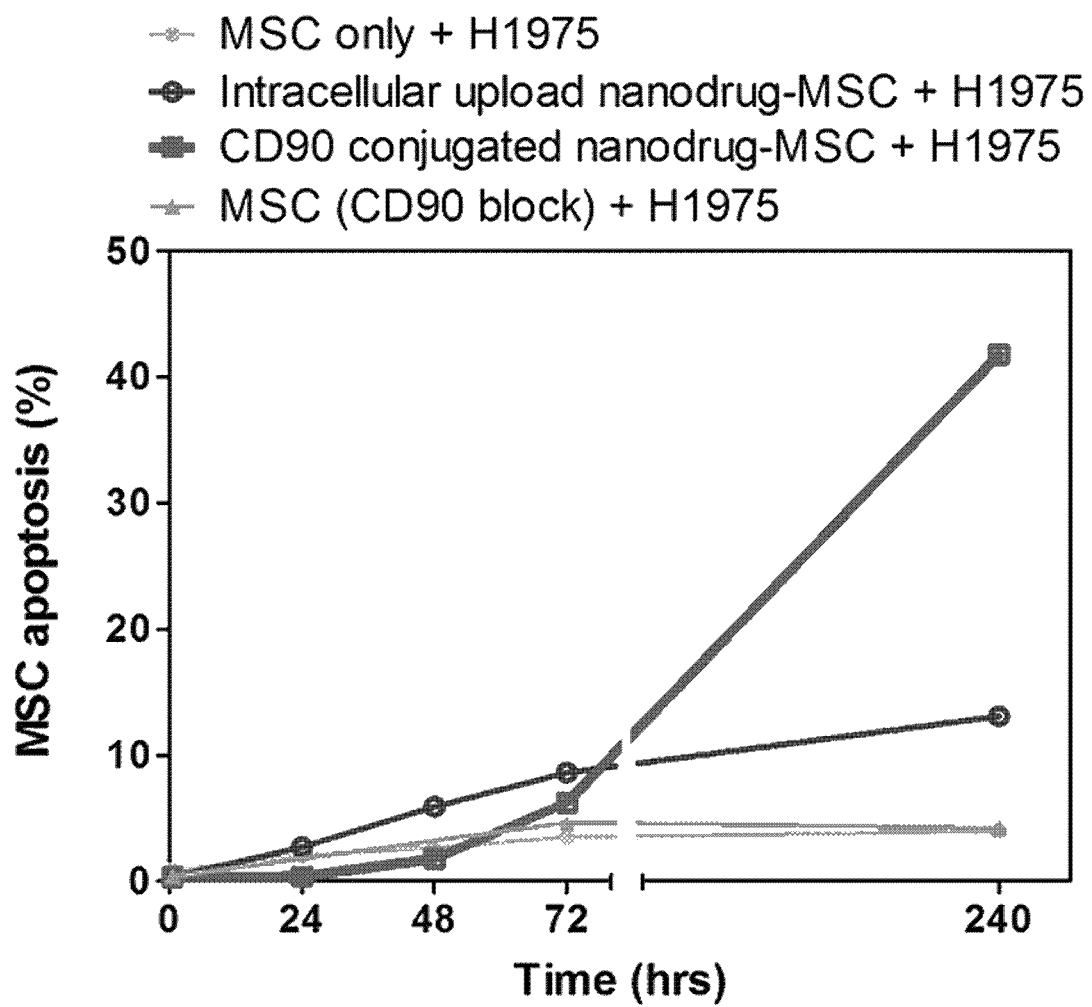
FIG. 17 is a graph analyzing the apoptosis ability of stem cells themselves of an MSC badge treatment group, MSC treatment group, MSC intracellular CNT-DOX uploading experimental group, MSC conjugation CNT-DOX experimental group, and control group.

As a result, it was found that the stem cell-nano anticancer drug complex has an ability to kill the lung cancer cells for a long time (240 hours) compared to the glass MSC (BM-MSC) and the experimental group in which nano anticancer drug is loaded in stem cells (FIGS. 15 and 16), and it was observed that apoptosis significantly increased in the period after 72 hours to 240 hours (FIG. 17).

Experimental Example 7: Calcium Signal Transduction Analysis between Nano Anticancer Drug Loading Experimental Group in Stem Cell and Cancer Cell of Stem Cell-Nano Anticancer Drug Complex After treatment of stem cell-nano anticancer drug complex functionally optimized according to an embodiment of the present invention in cancer cells, changes in intracellular calcium signaling in lung cancer cells (H1975) were compared and analyzed.

Specifically, lung cancer cells (H1975, 4×10$^5$) were treated with a stem cell-nano anticancer drug complex (MSC-CD90-mwCNT-DOX) and cultured on a coverslip for 48 hours, and then 0.05% Pluronic F-127 containing 4 μM of Fura-2 was reacted together in the dark at room temperature for 15 minutes in physiological saline, and using fluorescence microscopy, changes in intracellular calcium signaling in lung cancer cells after treatment of the stem cell-nano anticancer drug complex (MSC-CD90-mwCNT-DOX) and the experimental group in which nano anticancer drug is loaded in stem cells were confirmed at excitation/emission fluorescence wavelengths of 340/510 nm, and changes were analyzed using the MetaFluor system.

Figure 19:
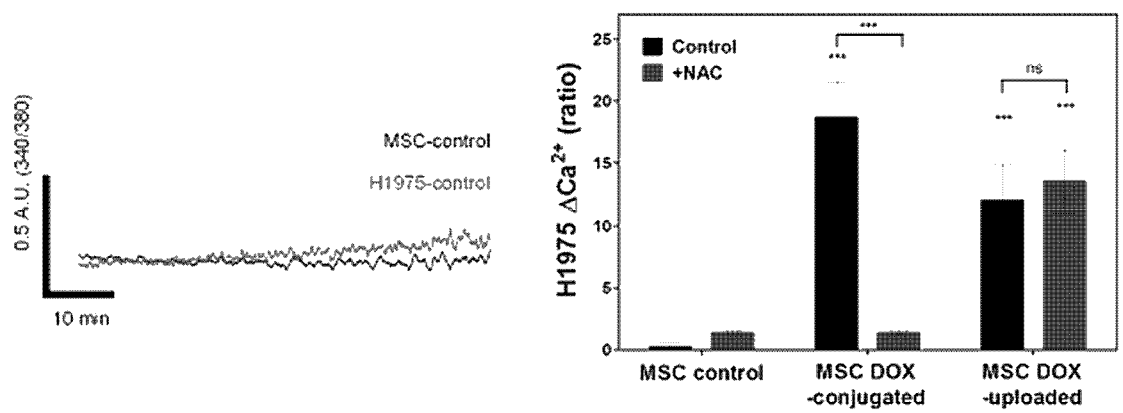
FIG. 19 is a graph analyzing a change in intracellular calcium signal transduction in the stem cell-nano anticancer drug complex and the MSC control group loaded with the nano anticancer drug in the stem cell or bound to the membrane protein of the stem cell.
Figure 20:
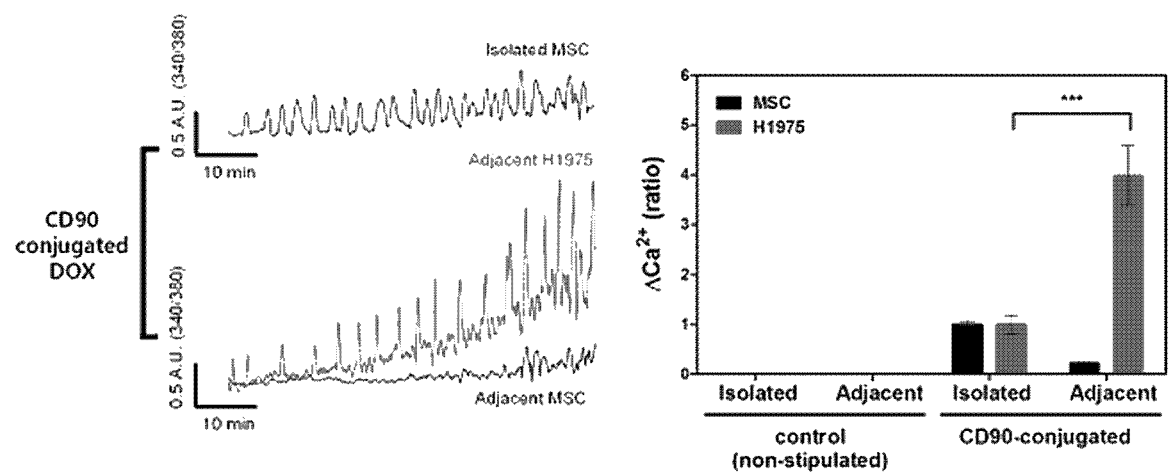
FIG. 20 is a diagram analyzing the relationship between the stem cell-nano anticancer drug complex and the MSC control group loaded with the nano anticancer drug in the stem cell and bound to the membrane protein of the stem cell after being treated with the lung cancer cell line (H1975), and graphs of changes in calcium signal transduction between the respective cells.
Figure 21:
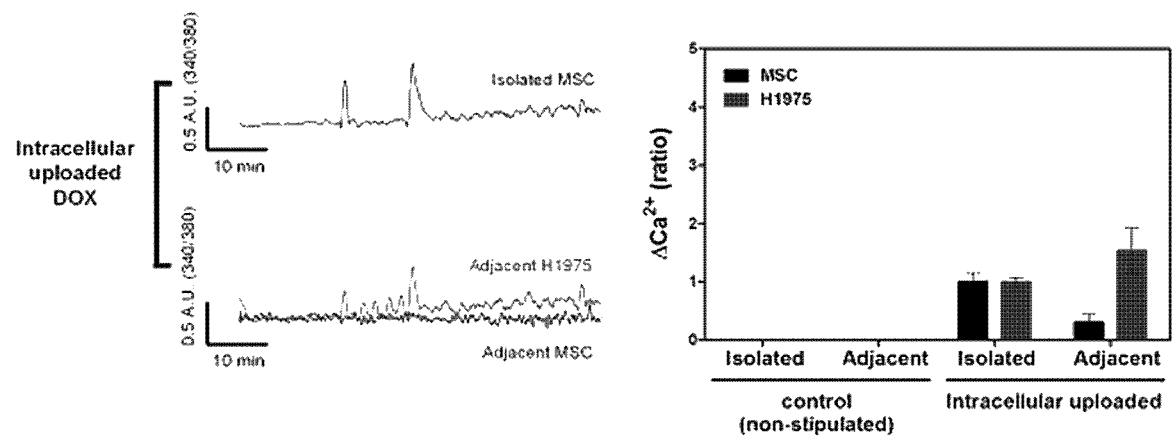
FIG. 21 is a diagram analyzing the relationship between the stem cell-nano anticancer drug complex and the MSC control group loaded with the nano anticancer drug in the stem cell and bound to the membrane protein of the stem cell after being treated with the lung cancer cell line (H1975), and graphs of changes in calcium signal transduction between the respective cells.

As a result, after treating the stem cell-nano anticancer drug complex (MSC-CD90-mwCNT-DOX), the intracellular calcium signaling change of the lung cancer cells was the highest compared to the experimental group in which nano anticancer drug is loaded in the stem cell, and thus was found to have the highest effect on the apoptosis of lung cancer cells (FIGS. 19 to 21).

Experimental Example 8: Verification of Possibility of Reverse Differentiation of MSC According to an embodiment of the present invention, the possibility of retrograde differentiation (cancer tumorigenesis) in cancer of MSC remaining after cancer cell death of the stem cell-nano anticancer drug complex was verified. Specifically, the experimental group and the stem cell-nano anticancer drug complex (MSC-CD90-mwCNT-DOX) loaded with glass MSC (BM-MSC) and stem cell at a ratio of 4×10$^5$ cells were cultured with 4×10$^5$ lung cancer cells (H1975) for a long period (240 hours), stained with cancer cell specific markers (CD31, 34), and then analyzed for expression levels using FACS to analyze the expression of MSC reverse differentiation and thereby investigate the possibility of reverse differentiation of MSC.

Figure 18:
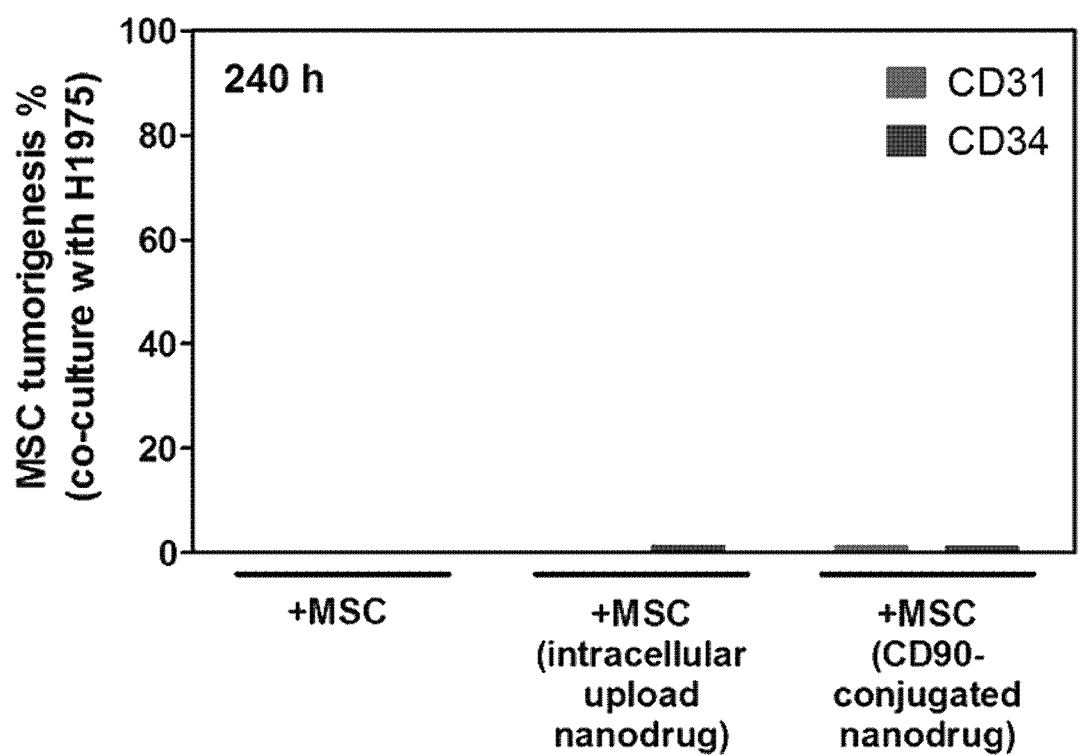
FIG. 18 is a graph analyzing the results of treatment with a lung cancer cell line for 240 hours in MSC badge treatment group, MSC treatment group, MSC intracellular CNT-DOX uploading experimental group, MSC conjugation CNT-DOX experimental group and control group, 4 is a graph showing retrodifferentiation of stem cells into cancer cells using proteins (CD31, 34).

As a result, it was confirmed that the stem cell-nano anticancer drug complex (MSC-CD90-mwCNT-DOX) that remains even after being treated for a long time and undergoing apoptosis does not undergo reverse differentiation to cancer (FIG. 18).

Experiment 9: Manufacture and Confirmation of Tumor Animal Model

In order to ascertain the apoptosis effect of cancer cells of the stem cell-nano anticancer drug complex according to an embodiment of the present invention from the in vivo animal model by a luminescence analysis method through luciferase activity, stably fluorescent/luminescent A549 non-small cell lung cancer cell line (A549-Luciferase-RFP) was constructed and a tumor mouse model was established.

Figure 22:
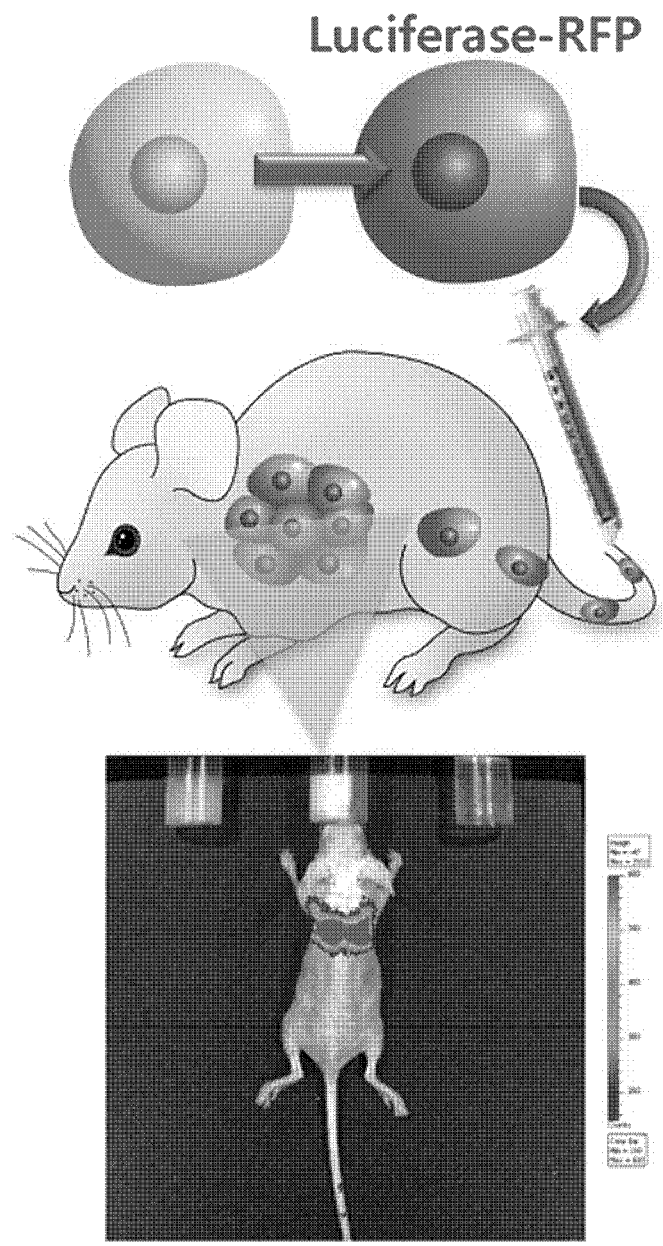
FIG. 22 is a schematic diagram showing schematically the establishment and validation process of a lung tumor model after tumor cell injection that emits luciferase-RFP fluorescence to nude mice.

Specifically, in order to prepare fluorescent/luminescent cells, 2×10$^3$ lentiviruses per 2×10$^3$ A549 lung cancer cells were introduced and transfection was carried out for 24 hours, and 2 to 3 days after culturing fluorescence expression was checked with a confocal fluorescence microscope, growth was continued in a medium containing puromycin antibiotics for about 2 to 3 weeks, and finally, stable cell lines were selected. Since the fluorescent/luminescent cell line stably expresses luciferase, when injecting luciferin as a substrate into mice via intravenous injection, the bioluminescence due to luciferase activity can be detected via the IVIS imaging apparatus in the presence of cancer cells. Thus, it is possible to quickly measure changes in the size of cancer cells through IVIS imaging. Subsequently, female (n=20) BALB/c nude mice (20 g, Experimental Animal Lab. of Gil-yeo Lee Cancer and Diabetes Institute, Gacheon University), were bred in ad-libitum feeding conditions in which the temperature was regulated and the light cycle was 6:00-18:00. In order to produce a tumor animal model, a non-small cell lung cancer strain (A549) cancer cell and a non-small cell lung cancer strain expressing luciferase-RFP fluorescence (A549-luciferase-RFP) were administered IV (intravenously)/c mice (2×10$^6$ cells) to generate lung tumors, and whether lung cancer was formed after 1, 2 and 3 weeks was confirmed using an animal fluorescence imaging apparatus (IVIS Spectrum In Vivo Imaging System, Perkinelmer). After 6 weeks, the mouse was sacrificed and the lung tissue was collected to make a paraffin tissue slide, and whether lung cancer was formed was confirmed through immunohistochemistry (FIG. 22).

Figure 23:
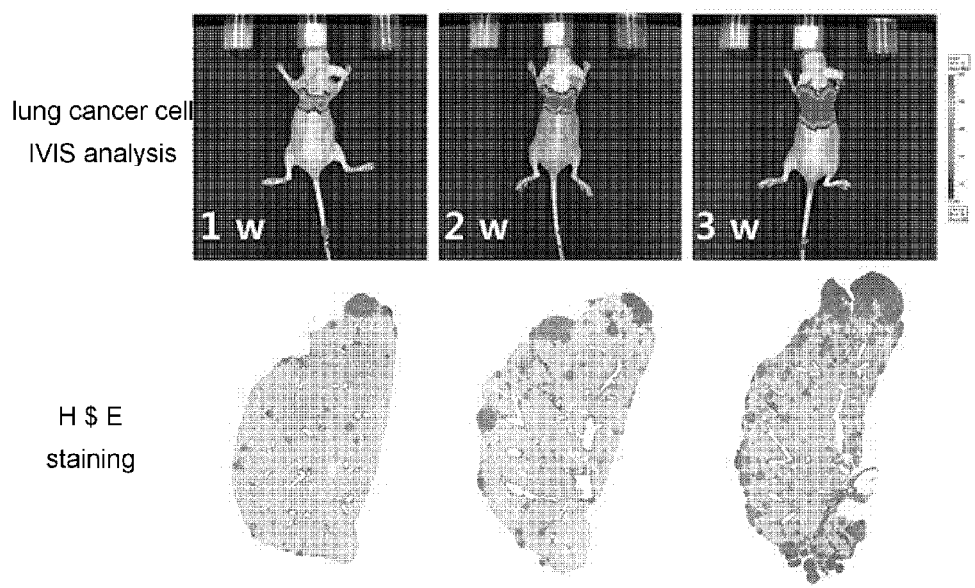
FIG. 23 is an image confirmed through fluorescence imaging apparatus (IVIS in vivo imaging system) and lung tissue staining after tumor cell injection into a lung tumor model mouse.
Figure 24:
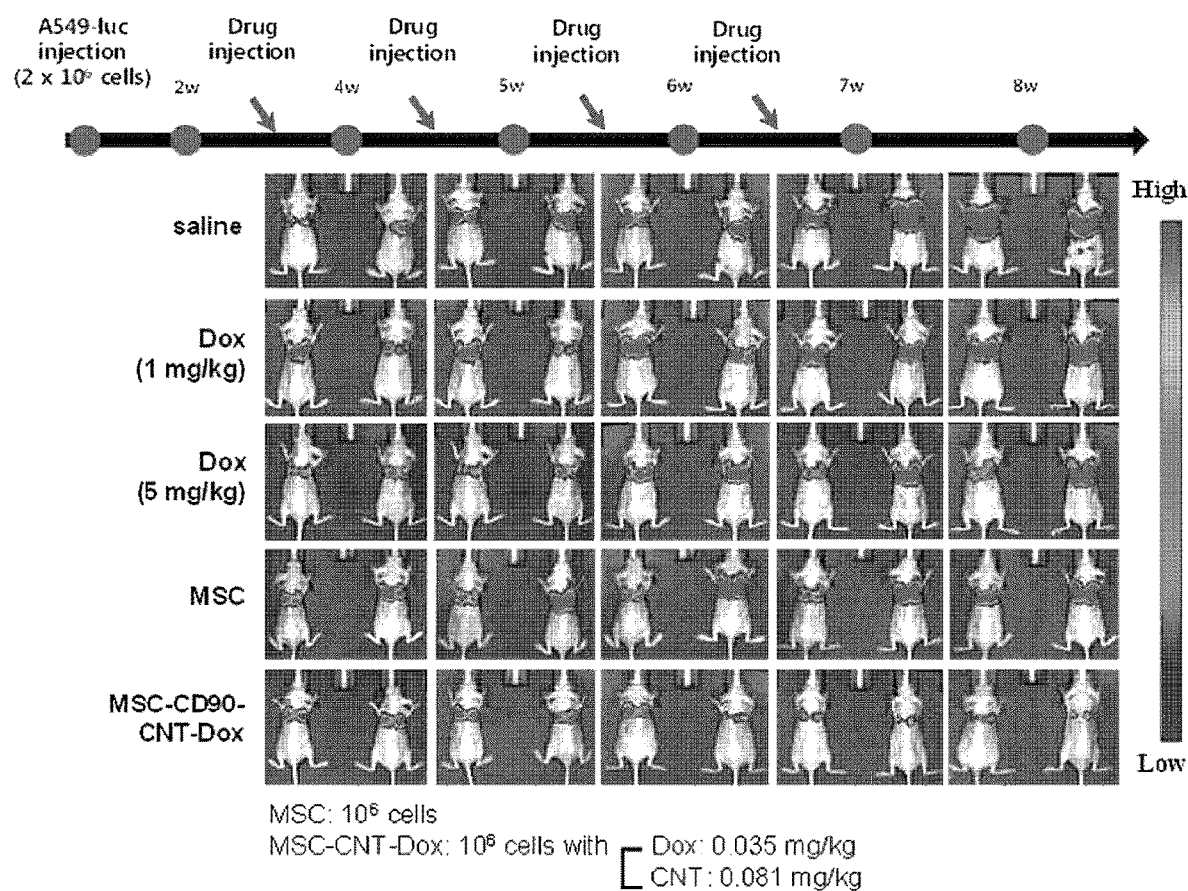
FIG. 24 is a graph showing whether or not fluorescent lung tumor is generated by administration of a stem cell-nano anticancer drug complex (hMSC-CD90-mwCNT-DOX) prepared according to an embodiment of the present invention in a fluorescence imaging apparatus It is a photograph observed.

As a result, it was confirmed that lung tumor was produced in the tumor animal model 2 weeks after the administration of the lung cancer cell line (FIG. 23).

Experimental Example 10: Analysis of Lung Tumor Suppressing Effect of Stem Cell-Nano Anticancer Drug Complex According to an embodiment of the present invention, the anti-tumor efficacy of a stem cell-nano anticancer drug complex was analyzed from an in vivo animal model.

Specifically, using in vivo fluorescence imaging, the cancer cell apoptosis effect of the stem cell-nano anticancer drug complex was confirmed using the IVIS animal fluorescence imaging system in the A549-luciferase-RFP tumor mouse model that fluoresces/emits. First, 2 weeks after injection of luciferase-RFP fluorescent lung cancer cells (H1975, A549) into nude mice, doxorubicin anticancer drug (5 mg/kg), free MSC (2×10$^6$ cells) and stem cell-nano anticancer drug complex (2×10$^6$ cells, 0.06 mg/kg) was injected intravenously twice at 5-day intervals, and 1 hour before measurement, luciferin 150 mg/kg IV injection was performed to activate luciferase, and then, using a fluorescence imaging apparatus, changes in lung cancer cell (H1975) fluorescence were analyzed over time.

Immunochemistry of the tissues was confirmed by injecting tumor cells into lung tumor nude mice and doxorubicin antitumor agent (low concentration: 0.02 mg/kg, high concentration: 5 mg/kg), carbon nano anticancer drug (low concentration: (Low concentration: 1×10$^6$ cells, 0.02 mg/kg; high concentration: 3×10$^6$ cells, 0.06 mg/kg) were administered to a free MSC (1×10$^6$ cells) and a stem cell-nano anticancer drug complex After four intravenous injections at 5-day intervals, the mice were sacrificed and the lung tissue was extracted to make a paraffin tissue slide, and then immunochemical tissue analysis was performed to determine the effect of the stem cell-nano anticancer drug complex.

Figure 25:
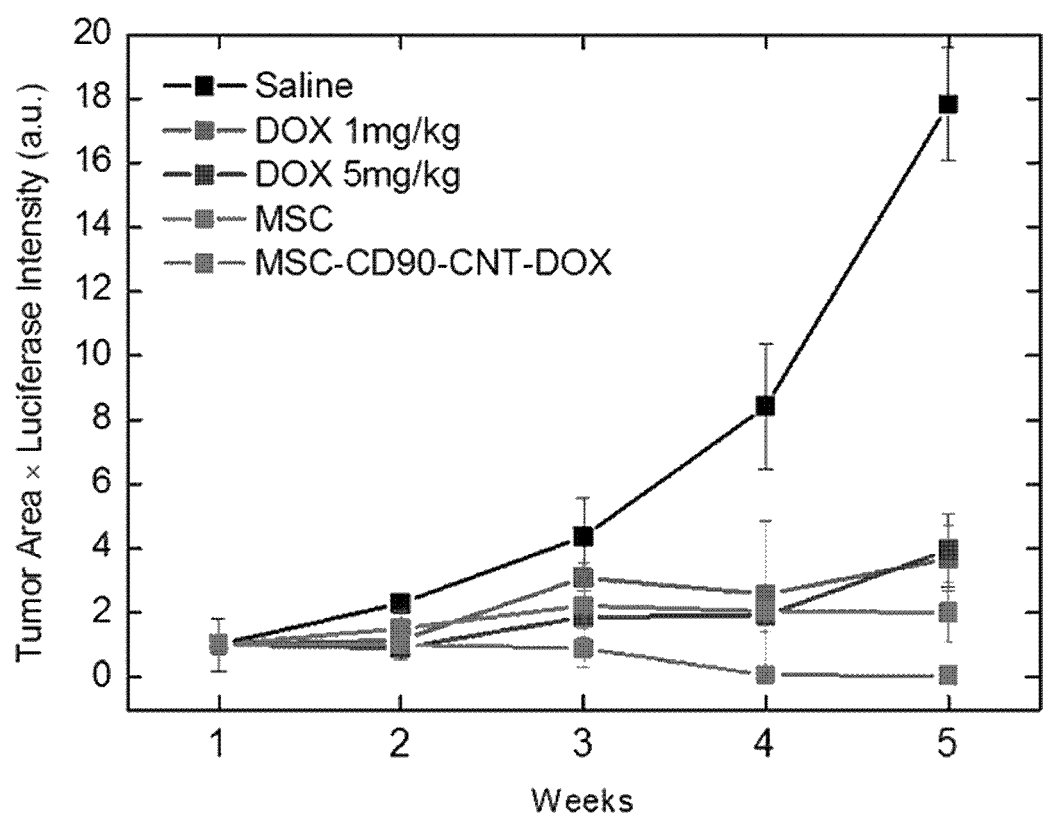
FIG. 25 is a graph of fluorescence intensity observed after administration of the stem cell-nano anticancer drug complex (hMSC-CD90-mwCNT-DOX) prepared according to an embodiment of the present invention.
Figure 26:
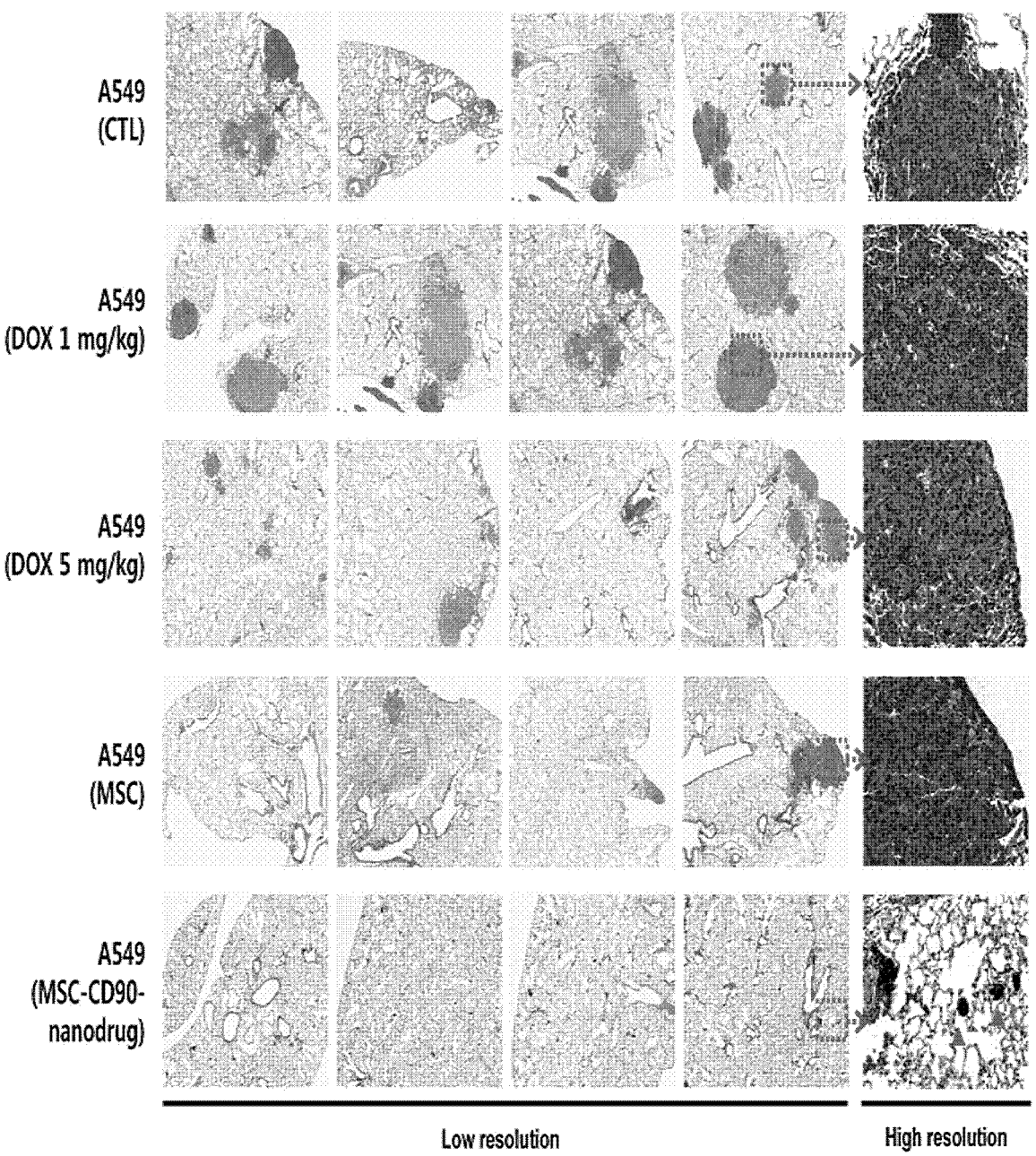
FIG. 26 shows that administration of a stem cell-nano anticancer drug complex (hMSC-CD90-mwCNT-DOX) prepared according to an embodiment of the present invention suppressed production of lung tumor. H & E: histochemical staining.

As a result, it was shown that administration of the stem cell-nano anticancer drug complex (hMSC-CD90-mwCNT-DOX) effectively suppresses luciferase-RFP fluorescence emitting lung tumor (FIG. 25). As a result of performing tissue immunochemistry, it was found that administration of the stem cell-nano anticancer drug complex (hMSC-CD90-mwCNT-DOX) effectively inhibited lung tumor formation (FIG. 26).

Figure 27:
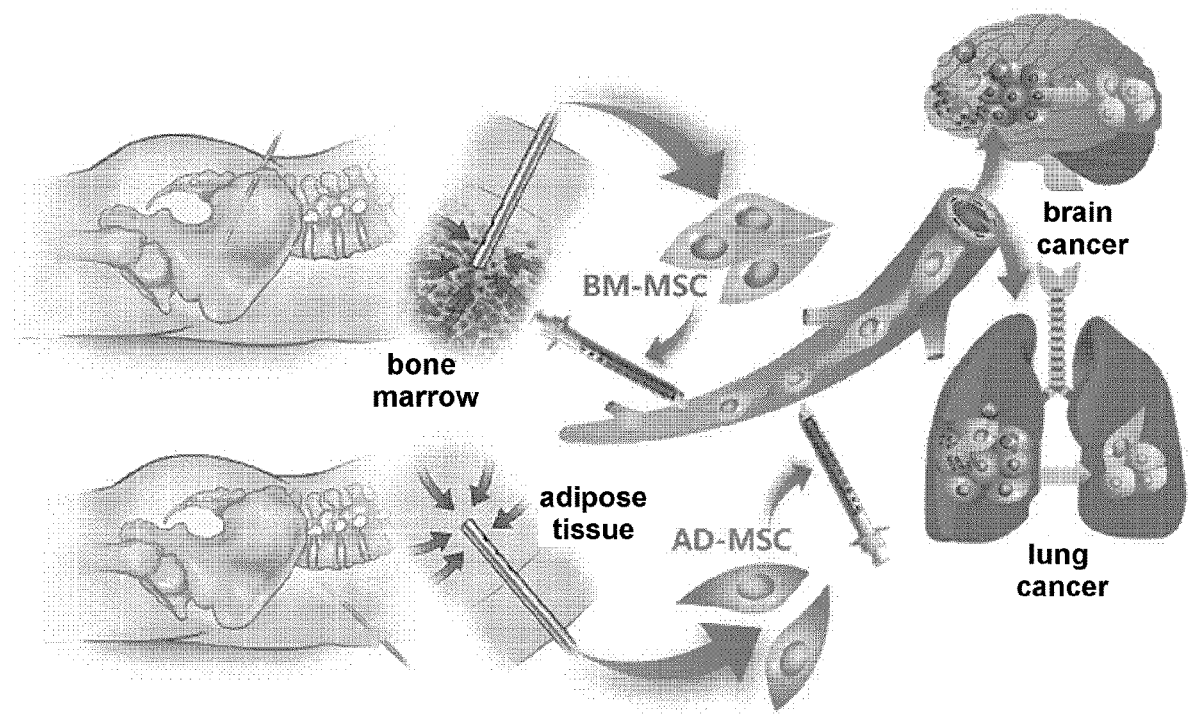
FIG. 27 is a diagram schematically showing the application process of a stem cell-nano anticancer drug complex (hMSC-CD90-mwCNT-DOX, hMSC-CD90-Au-DOX) selectively targeting a specific cancer.

In conclusion, the stem cell-nano anticancer drug complex (hMSC-CD90-mwCNT-DOX) according to an embodiment of the present invention can be used as an anticancer drug capable of maximizing the efficacy of anticancer drugs and minimizing side effects such as toxicity by loading nano anticancer drugs exhibiting the effect of anticancer drugs on the surface of MSC having excellent migration ability to cancer cells at low concentrations, and can be applied as a stem cell-nano anticancer drug that maximizes the efficacy of anticancer drugs of various cancers by selecting specific stem cells by type of cancer (FIG. 27).

Although the present invention has been described with reference to specific embodiments, it is not limited thereto. Therefore, it will be readily understood by those skilled in the art that various modifications and changes can be made thereto without departing from the spirit and scope of the present invention defined by the appended claims.

What is claimed is:

1. A mesenchymal stem cell-nano anticancer drug complex comprising,
a carbon nanotube (CNT) loaded with an anticancer drug attached to a surface of a mesenchymal stem cell,
wherein the CNT is bound to an antibody, a functional fragment of the antibody or an antibody mimetic,
wherein the antibody, the functional fragment of the antibody or the antibody memetic binds to CD90 on the surface of the mesenchymal stem cell.

2. The complex of claim 1, wherein the functional fragment of the antibody is Fab, F(ab')2, Fab', scFv, Fv, variable domain of camelid heavy chain ($V_H$H), sdAb, diabody, or triabody.

3. The complex of claim 1, wherein the antibody mimetic is Affibody, Affilin, Affitin, Anticalin, Avimer, DARPin, Fynomer, monobody, variable lymphocyte receptor (VLR), or repebody.

4. The complex of claim 1, wherein the weight ratio of the carbon nanotube to the anticancer drug in the complex is in 1:1 to 1:3.

5. The complex of claim 1, wherein the anticancer drug is doxorubicin, paclitaxel, ABT737, 5-fluorouracil, BCNU, CCNU, 6-mercaptopurine, nitrogen mustard, cyclophosphamide, vincristine, vinblastine, cisplatin, methotrexate, cytarabine, thiotepa, busulfan, or procarbazine.

6. The complex of claim 1, wherein the mesenchymal stem cell is an adipose stem cell or an umbilical cord stem cell.

7. A pharmaceutical anticancer composition comprising the mesenchymal stem cell-nano anticancer drug complex of claim 1 as an active ingredient.

8. A method for treating cancer, comprising administering a therapeutically effective amount of the mesenchymal stem cell-nano anticancer drug complex of claim 1 to a subject suffering from cancer.

9. A method for preparing the stem cell-nano anticancer drug complex of claim 1, comprising:
preparing a carboxylated nanoparticle by introducing a carboxyl group (—COOH) on the surface of a nanoparticle;
preparing an EDC {1-Ethyl-3-(3-dimethylaminopropyl) carbodiimide} linker bound nanoparticle by linking the EDC to the carboxylated nanoparticle;
binding an anticancer drug and an antibody, a functional fragment of the antibody or an antibody mimetic that specifically binds to a stem cell surface marker protein to the EDC linker bound nanoparticle covalently; and
attaching an anticancer drug and antibody, a functional fragment of the antibody, or an antibody mimetic specific to the stem cell surface marker protein bound nanoparticle to the stem cell.

10. The method of claim 9, wherein the preparing of the carboxylated nanoparticle is carried out by an acid treatment process of treating the carbon nanotube with acid.

11. The method of claim 10, further comprising an ultrasonic treatment process of treating acid-treated carbon nanotube with ultrasonic waves.

12. The complex of claim 1, wherein the carbon nanotube is a multi-walled carbon nanotube.

13. The complex of claim 12, wherein the multi-walled carbon nanotube has a diameter of 5 to 50 nm.

14. The complex of claim 1, wherein the weight ratio of the carbon nanotube to the anticancer drug in the complex is in 1:1 to 1:3.

* * * * *